US011834483B2

United States Patent
Lopes et al.

(12) 
(10) Patent No.: US 11,834,483 B2
(45) Date of Patent: Dec. 5, 2023

(54) IMMUNOSTIMULATORY AGENTS IN COMBINATION WITH ANGIOGENESIS INHIBITORS

(71) Applicant: Alkermes Pharma Ireland Limited, Dublin (IE)

(72) Inventors: Jared Lopes, Wilmington, MA (US); Heather C. Losey, Lexington, MA (US); Raymond J. Winquist, Marshfield, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 17/231,309

(22) Filed: Apr. 15, 2021

(65) Prior Publication Data

US 2021/0347837 A1    Nov. 11, 2021

Related U.S. Application Data

(60) Provisional application No. 63/165,391, filed on Mar. 24, 2021, provisional application No. 63/010,185, filed on Apr. 15, 2020.

(51) Int. Cl.
*C07K 14/47* (2006.01)
*C07K 16/22* (2006.01)
*A61P 35/00* (2006.01)
*A61K 39/00* (2006.01)
*A61K 38/00* (2006.01)

(52) U.S. Cl.
CPC .......... *C07K 14/4705* (2013.01); *A61P 35/00* (2018.01); *C07K 16/22* (2013.01); *A61K 38/00* (2013.01); *A61K 2039/505* (2013.01); *A61K 2039/542* (2013.01); *C07K 2319/30* (2013.01)

(58) Field of Classification Search
CPC ..... C07K 14/4705; C07K 16/22; A61P 35/00; A61K 38/00; A61K 2039/505; A61K 2039/542
See application file for complete search history.

(56) References Cited

U.S. PATENT DOCUMENTS

| | | | | |
|---|---|---|---|---|
| 9,359,415 B2 * | 6/2016 | Alvarez | .................. | A61P 25/00 |
| 9,844,582 B2 * | 12/2017 | Wittrup | .................. | A61K 45/06 |
| 10,407,481 B2 * | 9/2019 | Alvarez | .................... | A61P 5/00 |
| 11,246,906 B2 * | 2/2022 | Losey | ..................... | A61P 35/00 |
| 11,248,050 B2 * | 2/2022 | Losey | ............. | A61K 39/39558 |
| 2013/0336924 A1 * | 12/2013 | Alvarez | .................. | A61P 17/02 |
| | | | | 435/254.2 |
| 2017/0044228 A1 | 2/2017 | Alvarez | | |
| 2019/0241638 A1 | 8/2019 | Bernett et al. | | |
| 2021/0163596 A1 | 6/2021 | Losey et al. | | |

FOREIGN PATENT DOCUMENTS

| | | |
|---|---|---|
| CA | 3094329 A1 | 2/2020 |
| WO | WO 2012/154935 A1 | 11/2012 |
| WO | WO 2020/146773 A1 | 7/2020 |

OTHER PUBLICATIONS

Ferrara et al., Biochem Biophys Res Com 333:328-335 (2005) (Year: 2005).*
Matsuki et al., Cancer Science 108(4): 763-771 (2017) (Year: 2017).*
Hernandez et al., Nat Rev Immunology, vol. 22: 614-628 (2022) (Year: 2022).*
International Search Report and Written Opinion for International Application No. PCT/US2021/027503, dated Sep. 23, 2021, 11 pages.
Lopes et al., "ALKS 4230: a novel engineered IL-2 fusion protein with an improved cellular selectivity profile for cancer immunotherapy", *Journal for ImmunoTherapy of Cancer* 8:e000673 (2020).

* cited by examiner

*Primary Examiner* — Julie Wu
*Assistant Examiner* — Francesca Edgingtongiordan
(74) *Attorney, Agent, or Firm* — LATHROP GPM LLP; Michael Spellberg

(57) ABSTRACT

The invention provides compositions and methods of treating cancer in a patient with a combination therapy comprising administering to the patient a fusion protein of SEQ ID NO: 1, in combination with an angiogenesis inhibitor (e.g., an anti-VEGF antibody or lenvatinib).

16 Claims, 3 Drawing Sheets

Specification includes a Sequence Listing.

SEQUENCE LISTING

```
<160> NUMBER OF SEQ ID NOS: 3

<210> SEQ ID NO 1
<211> LENGTH: 303
<212> TYPE: PRT
<213> ORGANISM: Artificial Sequence
<220> FEATURE:
<223> OTHER INFORMATION: Human cpIL-2:IL-2R-alpha

<400> SEQUENCE: 1

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
```

```
                100              105              110
His Leu Gln Cys Leu Glu Glu Leu Lys Pro Leu Glu Glu Val Leu
        115              120              125

Asn Leu Ala Gln Gly Ser Gly Gly Ser Glu Leu Cys Asp Asp Asp
        130              135              140

Pro Pro Glu Ile Pro His Ala Thr Phe Lys Ala Met Ala Tyr Lys Glu
145              150              155              160

Gly Thr Met Leu Asn Cys Glu Cys Lys Arg Gly Phe Arg Arg Ile Lys
        165              170              175

Ser Gly Ser Leu Tyr Met Leu Cys Thr Gly Asn Ser Ser His Ser Ser
        180              185              190

Trp Asp Asn Gln Cys Gln Cys Thr Ser Ser Ala Thr Arg Asn Thr Thr
        195              200              205

Lys Gln Val Thr Pro Gln Pro Glu Glu Gln Lys Glu Arg Lys Thr Thr
        210              215              220

Glu Met Gln Ser Pro Met Gln Pro Val Asp Gln Ala Ser Leu Pro Gly
225              230              235              240

His Cys Arg Glu Pro Pro Trp Glu Asn Glu Ala Thr Glu Arg Ile
        245              250              255

Tyr His Phe Val Val Gly Gln Met Val Tyr Tyr Gln Cys Val Gln Gly
        260              265              270

Tyr Arg Ala Leu His Arg Gly Pro Ala Glu Ser Val Cys Lys Met Thr
        275              280              285

His Gly Lys Thr Arg Trp Thr Gln Pro Gln Leu Ile Cys Thr Gly
        290              295              300
```

<210> SEQ ID NO 2
<211> LENGTH: 309
<212> TYPE: PRT
<213> ORGANISM: Artificial Sequence
<220> FEATURE:
<223> OTHER INFORMATION: Mouse cpIL-2:IL-2R-alpha

<400> SEQUENCE: 2

```
Ser Lys Ser Phe Gln Leu Glu Asp Ala Glu Asn Phe Ile Ser Asn Ile
1               5                   10                  15

Arg Val Thr Val Val Lys Leu Lys Gly Ser Asp Asn Thr Phe Glu Cys
            20                  25                  30

Gln Phe Asp Asp Glu Ser Ala Thr Val Val Asp Phe Leu Arg Arg Trp
        35                  40                  45

Ile Ala Phe Cys Gln Ser Ile Ile Ser Thr Ser Pro Gln Gly Gly Ser
    50                  55                  60

Ser Ser Thr Gln Gln Gln Gln His Leu Glu Gln Leu Leu Met Asp
65              70                  75                  80

Leu Gln Glu Leu Leu Ser Arg Met Glu Asn Tyr Arg Asn Leu Lys Leu
                85                  90                  95

Pro Arg Met Leu Thr Phe Lys Phe Tyr Leu Pro Lys Gln Ala Thr Glu
            100                 105                 110

Leu Lys Asp Leu Gln Cys Leu Glu Asp Glu Leu Gly Pro Leu Arg His
        115                 120                 125

Val Leu Asp Leu Thr Gln Gly Ser Gly Gly Ser Glu Leu Cys Leu
        130                 135                 140

Tyr Asp Pro Pro Glu Val Pro Asn Ala Thr Phe Lys Ala Leu Ser Tyr
145                 150                 155                 160

Lys Asn Gly Thr Ile Leu Asn Cys Glu Cys Lys Arg Gly Phe Arg Arg
```

-continued

```
                165                 170                 175
Leu Lys Glu Leu Val Tyr Met Arg Cys Leu Gly Asn Ser Trp Ser Ser
            180                 185                 190

Asn Cys Gln Cys Thr Ser Asn Ser His Asp Lys Ser Arg Lys Gln Val
        195                 200                 205

Thr Ala Gln Leu Glu His Gln Lys Glu Gln Gln Thr Thr Asp Met
    210                 215                 220

Gln Lys Pro Thr Gln Ser Met His Gln Glu Asn Leu Thr Gly His Cys
225                 230                 235                 240

Arg Glu Pro Pro Pro Trp Lys His Glu Asp Ser Lys Arg Ile Tyr His
                245                 250                 255

Phe Val Glu Gly Gln Ser Val His Tyr Glu Cys Ile Pro Gly Tyr Lys
                260                 265                 270

Ala Leu Gln Arg Gly Pro Ala Ile Ser Ile Cys Lys Met Lys Cys Gly
                275                 280                 285

Lys Thr Gly Trp Thr Gln Pro Gln Leu Thr Cys Val Asp Gly Ser His
    290                 295                 300

His His His His His
305

<210> SEQ ID NO 3
<211> LENGTH: 20
<212> TYPE: PRT
<213> ORGANISM: Artificial Sequence
<220> FEATURE:
<223> OTHER INFORMATION: Signal sequence

<400> SEQUENCE: 3

Met Tyr Arg Met Gln Leu Leu Ser Cys Ile Ala Leu Ser Leu Ala Leu
1               5                   10                  15

Val Thr Asn Ser
            20
```

IMMUNOSTIMULATORY AGENTS IN COMBINATION WITH ANGIOGENESIS INHIBITORS

RELATED APPLICATIONS

This application claims the benefit of U.S. Provisional Application No. 63/010,185, filed Apr. 15, 2020, and U.S. Provisional Application No. 63/165,391, filed Mar. 24, 2021, the entire disclosures of which are hereby incorporated by reference.

SEQUENCE LISTING

The instant application contains a Sequence Listing which has been submitted electronically in ASCII format and is hereby incorporated by reference in its entirety. Said ASCII file, created on Apr. 15, 2021, is named 717261_ALW-3085_ST25.txt and is 6,059 bytes in size.

BACKGROUND

The fusion protein of SEQ ID NO: 1 is a human interleukin-2 (IL-2) variant fusion protein designed for selective binding of the intermediate-affinity interleukin-2 (IL-2) receptor, IL-2Rβγ. The selectivity of the fusion protein of SEQ ID NO: 1 is achieved through the stable fusion of circularly permuted (cp) IL-2 fused to the IL-2Rα chain (CD25) of the IL-2 receptor.

The fusion protein of SEQ ID NO: 1 has advantages over native IL-2 as a therapeutic in that its selective targeting and activation of IL-2Rβγ results in the selective activation of subsets of CD8+ T cells and NK cells, which can drive anti-tumor immune responses. The administration of the fusion protein of SEQ ID NO: 1 is beneficial to cancer patients as it reduces the immune suppressing effects of regulatory T-cells such as CD4+ T cells, while increasing CD8+ memory T-cells, thereby recruiting the patient's own immune system to eliminate cancer cells. The fusion protein of SEQ ID NO: 1 also exhibits lasting effects following administration, thereby further improving the patient's response to the treatment.

Undesirable or pathological angiogenesis has been associated with disease states including diabetic retinopathy, psoriasis, cancer, rheumatoid arthritis, and atheroma. Tumor angiogenesis, the formation of new blood vessels and their permeability is primarily regulated by (tumor-derived) vascular endothelial growth factor (VEGF), which acts via at least two different receptors: VEGF-R1 (Flt-1); and VEGF-R2 (KDR, Flk-1). The VEGF KDR receptor is highly specific for vascular endothelial cells (*Endocr. Rev.* 1992, 13, 18; *FASEB J.* 1999, 13, 9).

Many human tumors, especially gliomas and carcinomas, express high levels of VEGF and its receptors. High levels of VEGF have also been associated with an immunosuppressive tumor microenvironment and diminished responsiveness to, for example, high-dose recombinant human IL-2.

The current hypothesis is that the VEGF released by tumor cells stimulates the growth of blood capillaries and the proliferation of tumor endothelium in a paracrine manner, and through the improved blood supply, accelerate tumor growth. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis. However, a few problems have been noticed during the clinical development of angiogenesis inhibitors. In both preclinical and clinical settings, resistance to angiogenesis inhibitors occurs. In some patients, treatment with an angiogenesis inhibitor results in an initial response, followed by tumor progression (acquired resistance). In other patients, intrinsic resistance is being observed.

In the past few decades, the efforts to develop anti-angiogenic treatment mainly focus on inhibiting VEGF/VEGFR signaling pathway such as anti-VEGF antibody bevacizumab and anti-VEGFR2 antibody ramucirumab. Anti-VEGF/VEGFR single-target drugs often lead to transient responses; however, tumor progression happens because other pathways, such as the PDGF/PDGFR, FGF/FGFR, and ANGPT/Tie-2, provide potential escape mechanisms. Anti-angiogenic agents inhibiting multiple signaling pathways seem more promising; therefore, multiple pan-target agents have been developed One example of a compound that is capable of inhibiting multiple signaling pathways is lenvatinib. Lenvatinib, 4-[3-Chloro-4-(cyclopropylaminocarbonyl)aminophenoxy]-7-methoxy-6-quinolinecarboxamide, or a pharmaceutically acceptable salt (such as hydrochloride salt) thereof, has been developed as an anti-tumor agent also named "E7080". This compound is also disclosed in U.S. Pat. No. 7,253,286 as an angiogenesis inhibitor. Lenvatinib is a potent, selective inhibitor of the tyrosine kinase activity of vascular endothelial growth factor receptors types 1, 2, and 3 (VEGFR1-3); platelet derived growth factor receptors, types alpha and beta (PDGFRα/β) and fibroblast growth factor receptors, types 1, 2, and 3 (FGFR1-3) which are essential kinases for tumor growth, survival, migration and angiogenesis. By targeting these molecules, lenvatinib has the potential to simultaneously inhibit several angiogenesis pathways as well as signaling cascades that result in cell proliferation.

There remains a need for combination therapies that enhance and prolong antitumor immune responses compared to monotherapy and other combination therapies.

SUMMARY

The invention provides compositions, methods and combination treatment regimens for treating cancer in a patient by administering to the patient a combination of a fusion protein of SEQ ID NO: 1, and an angiogenesis inhibitor such as lenvatinib or an anti-VEGF antibody. In one aspect, the invention provides a method of treating cancer in a patient in need thereof, the method comprising: i) administering to the patient a therapeutically effective amount of a fusion protein of SEQ ID NO: 1, or a variant thereof that is at least 80% (e.g., 80%, 85%, 90%, 91%, 92%, 93%, 94%, 95%, 96%, 97%, 98%, 99%, or 100%) identical to SEQ ID NO: 1; and ii) administering to the patient a therapeutically effective amount of an angiogenesis inhibitor; wherein step (i) is carried out before, after or simultaneously with step (ii).

In another aspect, the invention provides a method of treating cancer in a patient in need thereof, the method comprising: i) administering to the patient a therapeutically effective amount of a fusion protein of SEQ ID NO: 1, or a variant thereof that is at least 80% (e.g., 80%, 85%, 90%, 91%, 92%, 93%, 94%, 95%, 96%, 97%, 98%, 99%, or 100%) identical to SEQ ID NO: 1; and ii) administering to the patient a therapeutically effective amount of an angiogenesis inhibitor selected from the group consisting of an antibody that binds specifically to VEGF or lenvatinib; wherein step (i) is carried out before, after or simultaneously with step (ii).

In another aspect, the invention provides a method of treating cancer in a patient in need thereof, the method comprising: i) administering to the patient a therapeutically effective amount of a fusion protein of SEQ ID NO: 1, or a variant thereof that is at least 80% (e.g., 80%, 85%, 90%, 91%, 92%, 93%, 94%, 95%, 96%, 97%, 98%, 99%, or 100%) identical to SEQ ID NO: 1; and ii) administering to the patient a therapeutically effective amount of lenvatinib; wherein step (i) is carried out before, after or simultaneously with step (ii).

In certain embodiments, an effective amount of the fusion protein of SEQ ID NO: 1 is an amount effective to activate the IL-2 intermediate receptor, IL-2Rβγ.

In certain embodiments, the fusion protein of SEQ ID NO: 1 is administered by intravenous or subcutaneous injection.

In certain embodiments, the angiogenesis inhibitor inhibits more than one receptor tyrosine kinase.

In certain embodiments, the angiogenesis inhibitor inhibits one or more of the following receptor tyrosine kinases: vascular endothelial growth factor receptors types 1, 2, and 3; platelet derived growth factor receptors, types alpha and beta platelet derived growth factor receptors, and fibroblast growth factor receptors, types 1, 2, and 3.

In certain embodiments, lenvatinib is administered orally.

In certain embodiments, the antibody that binds specifically to VEGF is administered intravenously.

In certain embodiments, the combination of steps (i) and (ii) results in an increase in CD8+ T cells in the tumors and spleen of the patient as compared to administration of a therapeutically effective amount of the fusion protein of SEQ ID NO: 1 as a monotherapy or administration of a therapeutically effective amount of the angiogenesis inhibitor as a monotherapy.

In certain embodiments, the increase in CD8+ T cells is at least 2-fold greater as compared to administration of a therapeutically effective amount of the fusion protein of SEQ ID NO: 1 as a monotherapy or administration of a therapeutically effective amount of the angiogenesis inhibitor as a monotherapy.

In certain embodiments, there is no increase in CD4+ T regulatory ($T_{regs}$) cells or conventional CD4+ T cells in the patient.

In certain embodiments, the combination of steps (i) and (ii) results in an increase in CD8+ T cells and dendritic cells in the tumors and spleen of the patient and a decrease in tumor associated macrophages in the patient as compared to administration of a therapeutically effective amount of the fusion protein of SEQ ID NO: 1 as a monotherapy or administration of a therapeutically effective amount of the angiogenesis inhibitor as a monotherapy.

In certain embodiments, the combination of steps (i) and (ii) results in an increase CD8+ T cells in the tumors and spleen of the patient as compared to administration of a therapeutically effective amount of the fusion protein of SEQ ID NO: 1 as a monotherapy or administration of a therapeutically effective amount of the angiogenesis inhibitor as a monotherapy.

In certain embodiments, the increase in CD8+ T cells is at least 2-fold greater as compared to administration of a therapeutically effective amount of the fusion protein of SEQ ID NO: 1 as a monotherapy or administration of a therapeutically effective amount of an angiogenesis inhibitor as a monotherapy.

In certain embodiments, the combination of steps (i) and (ii) results in an increase in CD8+ T cells and dendritic cells in the tumors and spleen of the patient and a decrease in tumor-associated macrophages in the patient as compared to administration of a therapeutically effective amount of the fusion protein of SEQ ID NO: 1 as a monotherapy or administration of a therapeutically effective amount of the angiogenesis inhibitor as a monotherapy.

In certain embodiments, the progression free survival of the patient is increased by at least about 10% as compared to administration of a therapeutically effective amount of the fusion protein of SEQ ID NO: 1 as a monotherapy or administration of a therapeutically effective amount of the angiogenesis inhibitor as a monotherapy.

In certain embodiments, the combination of steps (i) and (ii) results in greater expression of genes associated with cytotoxic immune cell function, T cell activation, and antigen presentation as compared to administration of a therapeutically effective amount of the fusion protein of SEQ ID NO: 1 as a monotherapy or administration of a therapeutically effective amount of the angiogenesis inhibitor as a monotherapy.

In certain embodiments, the combination of steps (i) and (ii) results in a decrease in Esm1 expression, and increased expression of Type I interferon and Type II interferon-associated genes as compared to administration of a therapeutically effective amount of the fusion protein of SEQ ID NO: 1 as a monotherapy or administration of a therapeutically effective amount of the angiogenesis inhibitor as a monotherapy.

In certain embodiments, the combination of steps (i) and (ii) results in changes in expression of a greater total number of genes as compared to administration of a therapeutically effective amount of the fusion protein of SEQ ID NO: 1 as a monotherapy or administration of a therapeutically effective amount of the angiogenesis inhibitor as a monotherapy.

In certain embodiments, the combination of steps (i) and (ii) results in greater expression of genes associated with cytotoxic immune cell function, T cell activation, and antigen presentation as compared to administration of a therapeutically effective amount of the fusion protein of SEQ ID NO: 1 as a monotherapy or administration of a therapeutically effective amount of the angiogenesis inhibitor as a monotherapy to a reference patient population.

In certain embodiments, the combination of steps (i) and (ii) results in a decrease in Esm1 expression, and increased expression of Type I interferon and Type II interferon-associated genes as compared to administration of a therapeutically effective amount of the fusion protein of SEQ ID NO: 1 as a monotherapy or administration of a therapeutically effective amount of the angiogenesis inhibitor as a monotherapy to a reference population.

over a period of days in mice implanted with MC38 tumor cells and thereafter treated with various doses of SEQ ID NO: 2, the murine surrogate of SEQ ID NO: 1 and/or lenvatinib.

Figure 3:
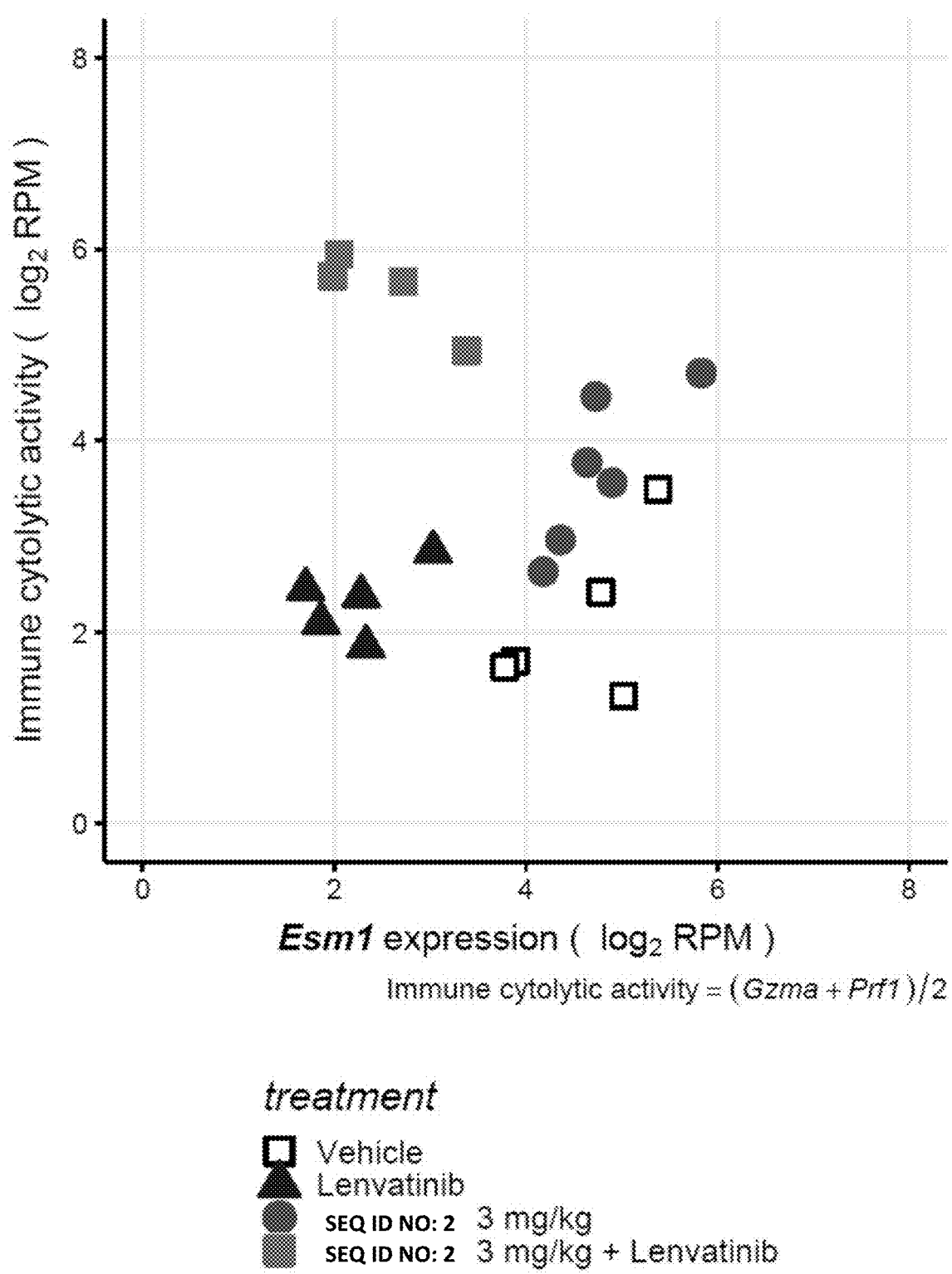

FIG. 3 depicts changes an angiogenesis gene expression (Esm1) and immune cytolytic activity gene expression (granzyme A and perforin genes) in mice implanted with MC38 tumor cells and thereafter treated with 3 mg/kg of SEQ ID NO: 2, the murine surrogate of SEQ ID NO: 1 and/or lenvatinib.

DETAILED DESCRIPTION

Definitions

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent. It is also noted that the term "comprising" is intended to be open and permits but does not require the inclusion of additional elements or steps. When the term "comprising" is used herein, the term "consisting of" is thus also encompassed and disclosed.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about wt. % to about 5 wt. %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, +9%, or ±10%, or more of the numerical value(s) being modified. In addition, the phrase "about 'x' to 'y'" includes "about 'x' to about 'y'".

The term "protein" or "peptide" as used herein refers to at least two or more amino acid residues linked together by peptide bond. The amino acid sequence in a protein or peptide is shown in the standard format, i.e., from amino terminus (N-terminus) to carboxyl terminus (C-terminus).

The term "fusion protein" designates a protein or peptide linked together with another protein or peptide by peptide bond between their respective N- and C-terminal amino acid residues or verse visa, or by insertion of the first protein or peptide into the internal region of the second protein or peptide by two peptide bonds at the N- and C-termini of the inserted protein or peptide. A peptide bond is a covalent chemical bond formed between carboxyl group of one amino acid and the amine group of another amino acid. A fusion protein is produced by expression of the fusion protein gene in an expression host, in which the coding sequence for the first protein or peptide is linked to the coding sequence of the second protein or peptide.

The "fusion protein of SEQ ID NO: 1" is also referred to herein as "cpIL-2:IL-2Rα" and is described in PCT application publication number, WO 2013/184942. The fusion protein of SEQ ID NO: 1 is a circularly permuted (cp) IL-2 variant fused to the extracellular domain of the IL-2Rα portion of the IL-2 receptor and has the following amino acid sequence:

(SEQ ID NO: 1)
SKNFHLRPRDLISNINVIVLELKGSETTFMCEYADETATIVEFLNRWIT

FSQSIISTLTGGSSSTKKTQLQLEHLLLDLQMILNGINNYKNPKLTRML

TFKFYMPKKATELKHLQCLEEELKPLEEVLNLAQGSGGGSELCDDDPPE

IPHATFKAMAYKEGTMLNCECKRGFRRIKSGSLYMLCTGNSSHSSWDNQ

CQCTSSATRNTTKQVTPQPEEQKERKTTEMQSPMQPVDQASLPGHCREP

PPWENEATERIYHFVVGQMVYYQCVQGYRALHRGPAESVCKMTHGKTRW

TQPQLICTG.

The invention also contemplates the use of a "variant" of the fusion protein of SEQ ID NO: 1 having an amino acid sequence having sequence identity that is about 75%, 80%, 85%, 90%, 91%, 92%, 93%, 94%, 95%, 96%, 97%, 98%, 99% or higher over a contiguous stretch of about 20 amino acids up to the full length of SEQ ID NO: 1. A variant of the SEQ ID NO: 1 may have a defined sequence identity as compared to SEQ ID NO: 1 over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a variant of the fusion protein of SEQ ID NO: 1 can comprise an amino acid sequence having at least about 75%, at least about 80%, at least about 85%, at least about 90%, at least about 95%, at least about 98%, or at least about 99%, amino acid sequence identity to a contiguous stretch of SEQ ID NO: 1 from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length of SEQ ID NO: 1.

The term "IL-2 therapy" includes administration of immunotherapy based on IL-2 and its associated biological functions as an immunotherapy including but not limited to maintenance of CD4$^+$ regulatory T cells and differentiation of CD4$^+$ T cells into a variety of subsets; promotion of CD8$^+$ T-cell and NK cell cytotoxicity activity, and modulation of T-cell differentiation programs in response to antigen, promoting naive CD4+ T-cell differentiation into T helper-1 (Th1) and T helper-2 (Th2) cells while inhibiting T helper-17 (Th17) differentiation. Therefore "IL-2 therapy" as used herein includes but is not limited to immunotherapy with rhIL-2 or a variant of rhIL-2 such as the Fusion Protein of SEQ ID NO: 1.

The terms "high dose IL-2" and "HD IL-2" include a dose of preferably, human recombinant interleukin-2 (IL-2) of about or at least about 600,000 International Units (IU)/kg of body weight (kg)/dose, or about or at least about 720,000 IU/kg/dose.

As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants. Preferably "patient" refers to a human subject who may seek or be in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable excipient" refers to a diluent, adjuvant, excipient or carrier with which a compound of the disclosure is administered. A pharmaceutically acceptable excipient is generally a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include water, any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The term "recombinant production" refers to the techniques for manipulating and combining two or more DNA sequences together that include recombination, PCR (polymerase chain reaction), in vitro mutagenesis, and direct DNA synthesis. These techniques are described in numerous published books and manuals, including the "Current protocols in molecular biology" (Ausubel eds. 2008. John Wiley & Son).

As used herein any form of administration or coadministration of a "combination", "combined therapy" and/or "combined treatment regimen" refers to at least two therapeutically active drugs or compositions which may be administered or co-administered", simultaneously, in either separate or combined formulations, or sequentially at different times separated by minutes, hours or days, but in some way act together to provide the desired therapeutic response.

As used herein, the term "parenteral" refers to dosage forms that are intended for administration as an injection or infusion and includes subcutaneous, intravenous, intra-arterial, intraperitoneal, intracardiac, intrathecal, and intramuscular injection, as well as infusion injections usually by the intravenous route.

The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. Preferably, an additional therapeutic agent is an anti-inflammatory agent.

The term "chemotherapeutic agent" refers to a compound or a derivative thereof that can interact with a cancer cell, thereby reducing the proliferative status of the cell and/or killing the cell for example, by impairing cell division or DNA synthesis, or by damaging DNA, effectively targeting fast dividing cells. Examples of chemotherapeutic agents include, but are not limited to, alkylating agents (e.g., cyclophosphamide, ifosfamide); metabolic antagonists (e.g., methotrexate (MTX), 5-fluorouracil or derivatives thereof); a substituted nucleotide; a substituted nucleoside; DNA demethylating agents (also known as antimetabolites; e.g., azacitidine); antitumor antibiotics (e.g., mitomycin, adriamycin); plant-derived antitumor agents (e.g., vincristine, vindesine, TAXOL®, paclitaxel, abraxane); cisplatin; carboplatin; etoposide; and the like. Such agents may further include, but are not limited to, the anti-cancer agents trimethotrexate (TMTX); temozolomide; raltitrexed; S-(4-Nitrobenzyl)-6-thioinosine (NBMPR); 6-benzyguanidine (6-BG); a nitrosoureas a nitrosourea (rabinopyranosyl-N-methyl-N-nitrosourea (Aranose), Carmustine (BCNU, BiCNU), Chlorozotocin, Ethylnitrosourea (ENU), Fotemustine, Lomustine (CCNU), Nimustine, N-Nitroso-N-methylurea (NMU), Ranimustine (MCNU), Semustine, Streptozocin (Streptozotocin)); cytarabine; and camptothecin; or a therapeutic derivative of any thereof.

The terms "treating" or "treatment" of a disease (or a condition or a disorder) as used herein refer to preventing the disease from occurring in a human subject or an animal subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and causing regression of the disease. With regard to cancer, these terms also mean that the life expectancy of an individual affected with a cancer may be increased or that one or more of the symptoms of the disease will be reduced. With regard to cancer, "treating" also includes enhancing or prolonging an anti-tumor response in a subject.

The phrase "therapeutically effective amount" or an "effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used. In reference to cancer or pathologies related to unregulated cell division, a therapeutically effective amount refers to that amount which has the effect of (1) reducing the size of a tumor (i.e., tumor regression), (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer. An "effective amount" is also that amount that results in desirable PD and PK profiles and desirable immune cell profiling upon administration of the therapeutically active compositions of the invention.

The term "therapeutically effective amount" in the specific context of administration of the fusion protein SEQ ID NO: 1 to a patient includes, but is not limited to, that amount of the fusion protein of SEQ ID NO: 1 that is an amount effective to activate the IL-2 intermediate receptor, IL-2Rβγ.

The term "therapeutically effective amount" in the specific context of administration of angiogenesis inhibitor such as lenvatinib to a patient includes, but is not limited to, that amount of angiogenesis inhibitor effective to inhibit the activity of one or more pro-angiogenic receptor tyrosine kinases including, but not limited to, vascular endothelial growth factor receptors types 1, 2, and 3 (VEGFR1-3); platelet derived growth factor receptors, types alpha and beta (PDGFRα/β) and fibroblast growth factor receptors, types 1, 2, and 3 (FGFR1-3) or any combination thereof.

"Progression free survival (PFS)," as used in the context of the cancers described herein, refers to the length of time during and after treatment of the cancer wherein tumor growth is halted, reduced or the tumor is eliminated entirely until the time when the tumor resumes growth, tumor progression or other tumors appear or until the death of the patient from any cause. The treatment may be assessed by objective or subjective parameters, including the results of a physical examination, neurological examination, or psychiatric evaluation. In preferred aspects, PFS may be assessed by blinded imaging central review and may further optionally be confirmed by overall response rate (ORR) or by blinded independent central review (BICR). An increase in PFS may be determined based on a comparison to, for example, one or more other patients not receiving the combination therapy of the invention or one or more patients receiving only one drug of the combination therapy i.e. a monotherapy, and may be expressed as a mean percentage. The specified timeframe may be compared between treatment regimens, for example a comparison may be made between the combination therapy of the invention and monotherapy using only one of the components of the combination therapy. The comparisons may also be made between combination therapies of other the same or different angiogenesis inhibitors and, for example, high dose human recombinant IL-2.

"Overall survival (OS)" may be assessed by OS rate at certain time points (e.g., 1 year and 2 years) by the Kaplan-Meier method and corresponding 95% CI will be derived based on Greenwood formula by study treatment for each tumor type. OS rate is defined as the proportion of participants who are alive at the time point. OS for a participant is defined as the time from the first dosing date to the date of death due to any cause. The specified timeframe may be compared between treatment regimens, for example a comparison may be made between the combination therapy of the invention and monotherapy using only one of the components of the combination therapy. The comparisons may also be made between combination therapies of other the same or different angiogenesis inhibitors and, for example, high dose human recombinant IL-2.

As used herein a "complete response" (CR) is the disappearance of all signs of cancer in response to treatment. Complete response may also be referred to herein as "total remission" or a "complete remission". The term Complete Response includes but is not limited to the identification of a complete response that is achieved within a specified timeframe. The specified timeframe may be compared between treatment regimens, for example a comparison may be made between the combination therapy of the invention and monotherapy using only one of the components of the combination therapy. The comparisons may also be made between combination therapies of the same or different angiogenesis inhibitors in, for example, reference patient populations and, for example, high dose human recombinant IL-2.

As used herein the term "partial response" (PR) means a decrease in the size of the tumor, or in the extent of cancer in the body in response to treatment. Partial response may also be referred to herein as a "partial remission". The term "partial response" includes but is not limited to the identification of a partial response that is achieved within a specified timeframe. The specified timeframe may be compared between treatment regimens in reference patient populations, for example a comparison may be made between the combination therapy of the invention and monotherapy using only one of the components of the combination therapy. The comparisons may also be made between combination therapies of the same or different angiogenesis inhibitors and, for example, high dose human recombinant IL-2.

The term "cancer", as used herein, shall be given its ordinary meaning, as a general term for diseases in which abnormal cells divide without control.

The term "reducing a tumor" or "tumor regression" as used herein refers to a reduction in the size or volume of a tumor mass, a decrease in the number of metastasized tumors in a subject, a decrease in the proliferative status (the degree to which the cancer cells are multiplying) of the cancer cells, and the like.

The terms "enhanced," "enhancing," "increasing," or increased in the context of a patient's response to the combination therapy of the invention, as used herein, refers to an improvement of any aspect of a patient's response to a combination therapy treatment disclosed herein including but not limited to: enhanced reduction in tumor size, enhanced PFS, enhanced CR, and enhanced OS as compared to a reference response. For example, an enhanced or increased response may comprise an increase in responsiveness of at least 5%, 10%, 15%, 20%, 25%, 30%, 35%, 40%, 45%, 50%, 55%, 60%, 65%, 70%, 75%, 80%, 85%, 90%, 95% or 98% or more as compared to reference response. A reference response may be, for example, the response of a patient or a population of patients to monotherapy using only one of the components of the combination therapy. Another reference response, for example, may be made between combination therapies of the same or different angiogenesis inhibitors and, for example, high dose human recombinant IL-2 in a patient or a population of patients.

As used herein, "enhancing" and "increasing" can also refer to enhancing or increasing the number of subjects who respond to a treatment such as a combination therapy comprising the fusion protein of SEQ ID NO: 1 and any one or more of the following: angiogenesis inhibitors, chemotherapy, drug-resistant immunocompetent cells, and immune checkpoint inhibitors. For example, an enhanced or increased response may refer to a total percentage of subjects who respond to a treatment wherein the percentage is of at least 5%, 10%, 15%, 20%, 25%, 30%, 35%, 40%, 45%, 50%, 55%, 60%, 65%, 70%, 75%, 80%, 85%, 90%, 95% or 98% or more.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., Remington: The Science and Practice of Pharmacy, 22nd Edition, Pharmaceutical Press, London, UK (2012).

As used herein the term "angiogenesis inhibitor" refers to a drug, compound, antibody or other agent that keeps new blood vessels from forming. In cancer treatment, angiogenesis inhibitors may prevent the growth of new blood vessels that tumors need to grow. Angiogenesis inhibitors include those agents that can target one or more signaling pathways associated with receptor tyrosine kinases (RTK). RTKs include, but are not limited to, vascular endothelial growth factor receptors types 1, 2, and 3 (VEGFR1-3); platelet derived growth factor receptors, types alpha and beta (PDGFRα/β) and fibroblast growth factor receptors (FGFR), types 1, 2, and 3 (FGFR1-3). Preferred angiogenesis inhibitors in accordance with the invention have broad target selectivity and are capable of simultaneous targeted inhibition of multiple RTKs and are referred to herein as "multiple receptor tyrosine kinase inhibitors".

One preferred multiple receptor tyrosine kinase inhibitor is lenvatinib, 4-[3-Chloro-4-(cyclopropylaminocarbonyl)aminophenoxy]-7-methoxy-6-quinolinecarboxamide (CAS #417716-92-8), or a pharmaceutically acceptable salt (such as hydrochloride salt). Lenvatinib is described in further detail in U.S. Pat. No. 7,253,286, incorporated herein by reference. Lenvatinib is represented by Formula I:

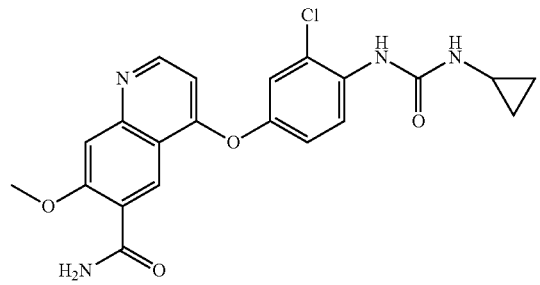

Formula I

"Vascular endothelial growth factor (VEGF)" is a signaling protein involved in the regulation of angiogenesis and vasculogenesis. VEGF binds to and activates a receptor tyrosine kinase, VEGFR, through transphosphorylation. Three VEGFR isoforms have been identified in humans.

"Vascular endothelial growth factor (VEGF)/vascular endothelial growth factor receptor (VEGFR)" inhibitors are agents that inhibit the activity of VEGF and VEGFR. VEGFR and VEGFR (a tyrosine kinase receptor) signaling modulates angiogenesis which involves making of new blood vessels from existing blood vessels. Abnormal angiogenesis is known to occur in cancer, degenerative eye conditions and other conditions that involve inflammation. Specific monoclonal antibodies can be used as VEGF inhibitors and particular tyrosine kinase inhibitors are used as VEGFR inhibitors. Vascular endothelial growth factor (VEGF)/vascular endothelial growth factor receptor (VEGFR) inhibitors are used to treat various types of cancers.

"VEGFR tyrosine kinase inhibitor" is a substance that blocks an enzyme needed to form blood vessels. Also called vascular endothelial growth factor receptor tyrosine kinase inhibitor. Lenvatinib is a VEGFR tyrosine kinase inhibitor.

"FGF receptor" belongs to a group of receptor tyrosine kinases. In the present invention, FGFR1, FGFR2, FGFR3, FGFR4 and FGFR5 are collectively referred to as an FGF receptor. Furthermore, a substance, which has a homology with the amino acid sequence of any one of FGFR1, FGFR2, FGFR3, FGFR4 and FGFR5 and has an FGF receptor activity (including a receptor whose function presently remains unknown but will be classified in the same family in future), is also included in the FGF receptor. The FGF receptor activity can be determined by detecting phosphorylation of the receptor by means of ELISA or Western blotting.

"FGF receptor inhibitor" refers to an inhibitor having an inhibitory activity against an FGF receptor. The FGF receptor inhibitor may have inhibitory activities against other receptor tyrosine kinases and other biological molecules as long as it has an inhibitory activity against an FGF receptor.

"Platelet derived growth factor (PDGF) receptor" belongs to a group of receptor tyrosine kinases. In the present invention, PDGFR-α and PDGFR-β are collectively referred to as PDGF receptor. Furthermore, a substance, which has a homology with the amino acid sequence of any one of PDGFR-α and PDGFR-β and has a PDGF receptor activity (including a receptor whose function presently remains unknown but will be classified in the same family in future), is also included in PDGF receptor. The PDGF receptor activity can be determined by detecting phosphorylation activity of the receptor by means of ELISA or Western blotting.

"PDGF receptor inhibitor" refers to an inhibitor having an inhibitory activity against PDGF receptor. The PDGF receptor inhibitor may have inhibitory activities against other receptor tyrosine kinases and other biological molecules as long as it has an inhibitory activity against PDGF receptor.

"RET kinase", which belongs to a group of receptor tyrosine kinases, is a functional receptor for a ligand of Glia cell-line Derived Neurotropic Factor (GDNF) family. In the present invention, furthermore, a substance, which has a homology with the amino acid sequence of RET kinase and has a RET kinase activity (including a receptor whose function presently remains unknown but will be classified in the same family in future), is also included in RET kinase. The RET kinase activity can be determined by detecting phosphorylation activity of the receptor by means of ELISA or Western blotting.

"RET kinase inhibitor" refers to an inhibitor having an inhibitory activity against RET kinase. The RET kinase inhibitor may have inhibitory activities against other receptor tyrosine kinases and other biological molecules as long as it has an inhibitory activity against RET kinase.

"KIT kinase", which is also referred to as c-Kit or an SCF receptor, belongs to a group of receptor tyrosine kinases. In the present invention, furthermore, a substance, which has a homology with the amino acid sequence of the KIT kinase and has a KIT kinase activity (including a substance whose function presently remains unknown but will be classified in the same family in future), is also included in KIT kinase.

"KIT kinase inhibitor" refers to an inhibitor having an inhibitory activity against KIT kinase. The KIT kinase inhibitor may have inhibitory activities against other receptor tyrosine kinases and other biological molecules as long as it has an inhibitory activity against KIT kinase. The KIT kinase activity can be determined by detecting phosphorylation activity of the receptor by means of ELISA or Western blotting method.

"EGF" refers to Epithelial Growth Factor and the "EGF inhibitor" refers to an inhibitor having inhibitory activity against signaling induced by binding of EGF to its receptor. The EGF inhibitor may have inhibitory activities against other biological molecules as long as it has an inhibitory activity against signaling induced by EGF.

"Integrin" is one of cell surface proteins mainly serving as a cell adhesion molecule. The structure is a heterodimer consisting of an α chain and a β chain. Up to present, 22 types of integrins consisting of different α chains and β chains in combination have found and form an integrin family. The "integrin inhibitor" refers to an inhibitor having an inhibitory activity against signaling induced by binding of integrin to its receptor, The integrin inhibitor may have inhibitory activities against other biological molecules as long as it has an inhibitory activity against signaling induced by integrin.

"Matrix metalloprotease" belongs to a group of zinc ion ($Zn^{2+}$)-dependent proteases involved in degradation of extracellular matrix. The matrix metalloprotease is known to degrade the basal membrane around blood vessels, thereby enhancing angiogenesis. The "matrix metalloprotease inhibitor" refers to an inhibitor having an inhibitory activity against matrix metalloprotease. The matrix metalloprotease inhibitor may have inhibitory activities against other biological molecules as long as it has an inhibitory activity against matrix metalloprotease.

The Fusion Protein of SEQ ID NO: 1

The invention provides combination therapy with the recombinant human IL-2 variant fusion protein of SEQ ID NO: 1, described in WO 2013/184942, which is a circularly permuted (cp) IL-2 variant fused to the extracellular domain of the IL-2Rα portion of the IL-2 receptor.

It is contemplated that fusion proteins that are closely related to SEQ ID NO: 1, such as those fusion proteins having sequence identities of about 80%, 85%, 90%, 91%, 92%, 93%, 94%, 95%, 96%, 97%, 98%, 99% or higher identity over a contiguous sequence of at least about amino acids up to the full length of SEQ ID NO: 1 may also be suitable for administration in accordance with the methods of the invention.

The fusion protein of SEQ ID NO: 1 is designed to selectively bind to and activate the intermediate-affinity IL-2R, but not the high-affinity IL-2R. The IL-2Rα domain of the fusion protein of SEQ ID NO: 1 serves to sterically impede the binding of the fusion protein of SEQ ID NO: 1 to the high-affinity IL-2R yet still allow binding to the intermediate-affinity IL-2R.

In vitro and in vivo nonclinical pharmacodynamic (PD) data support selective signaling through the intermediate-affinity IL-2 receptor by the fusion protein of SEQ ID NO: 1, leading to the activation and expansion of effector cells such as NK cells and CD8+ T cells, while minimizing the activation and expansion of immunosuppressive $T_{regs}$. Additionally, in vivo in mice, the mouse surrogate of fusion protein of SEQ ID NO: 1 displays improved tolerability relative to recombinant human IL-2 (rhIL-2) at doses that elicit equivalent or greater expansion of effector cells relative to $T_{regs}$.

First in human clinical data described in U.S. Patent Publication Number 20210038684A1 indicates that the fusion protein of SEQ ID NO: 1 activates expansion of CD8+ T cells and NK cells in a dose dependent manner in the absence of dose dependent activation of $T_{regs}$. Therefore, the fusion protein of SEQ ID NO: 1 can be dosed in human patients at a concentration that is comparative to high dose rhIL-2 to elicit equivalent or greater expansion of NK cells and CD8+ T cells as compared to, for example, high dose rhIL-2 but with far less (at least two-fold less) relative expansion of immunosuppressive Tregs as compared to high dose rhIL-2.

Methods for Combination Treatment Regimen

The invention provides methods for combination treatment regimens for treating cancer in a patient in need thereof. The methods of the invention comprise: i) administering to the patient a therapeutically effective amount of a fusion protein of SEQ ID NO: 1; and ii) administering to the patient a therapeutically effective amount of an angiogenesis inhibitor such as a multiple receptor tyrosine kinase inhibitor; wherein step (i) is carried out before, after or simultaneously with step (ii).

The invention also provides combination treatment regimens for treating cancer in a patient comprising: i) administering to the patient a therapeutically effective amount of variant of the fusion protein of SEQ ID NO: 1 wherein the variant has an amino acid sequence that is about 80%, 85%, 90%, 91%, 92%, 93%, 94%, 95%, 96%, 97%, 98%, or 99% identical to SEQ ID NO: 1 over the full length SEQ ID NO: 1; and ii) administering to the patient a therapeutically effective amount of an angiogenesis inhibitor; wherein step (i) is carried out before, after or simultaneously with step (ii).

Preferably, an effective amount SEQ ID NO: 1 or variant thereof is an amount effective to activate the IL-2 intermediate receptor, IL-2Rβγ. Preferably, an effective amount of an angiogenesis inhibitor is an amount effective to inhibit tumor growth. Preferably an effective amount of an angiogenesis inhibitor is an amount effective to inhibit the activity of one or more RTKs including but not limited to, vascular endothelial growth factor receptors types 1, 2, and 3 (VEGFR1-3); platelet derived growth factor receptors, types alpha and beta (PDGFRα/β) and fibroblast growth factor receptors, types 1, 2, and 3 (FGFR1-3).

With respect to administering steps (i) and (ii), these administering steps can be performed in either order (as well as simultaneously) and the invention is not limited in this regard. The administering step (i) may be carried out before administering step (ii). The administering step (ii) may be carried out before administering step (i). Both administering steps (i) and (ii) may be carried out simultaneously. Administering steps (i) and/or (ii) may be carried out repeatedly. Administering steps (i) and (ii) may be carried out only once.

A therapeutically effective amount of the fusion protein of SEQ ID NO: 1 in combination with an angiogenesis inhibitor may or may not be the same as a therapeutically effective amount of the fusion protein of SEQ ID NO: 1 when delivered as a monotherapy. However, so long as the combined treatment regimen provides the desired results, the amount of the fusion protein of SEQ ID NO: 1 used in the combined treatment regimen is deemed to be therapeutically effective. Generally, a therapeutically effective amount of the fusion protein of SEQ ID NO: 1 when combined with an angiogenesis inhibitor is an amount sufficient to activate the target intermediate IL-2 receptor, IL-2Rβγ. Activation of the IL-2Rβγ includes, for example, expansion of NK cells and CD8+ T cells. Preferably, an effective amount of SEQ ID NO: 1 or variant thereof is an amount effective to, for example, cause a dose dependent increase in circulating NK cells and CD8+ T cells in a patient with minimal, non-dose-dependent increase in circulating T regulatory (Treg) cells. Preferably, the increase in circulating NK cells and CD8+ T cells relative to the increase in circulating T regulatory (Treg) is greater in a patient administered the fusion protein of SEQ ID NO: 1.

One skilled in the art can determine that amount using standard assays such as the FACS analysis of cells or tissue treated with the fusion protein of SEQ ID NO: 1 or a combination therapy with an angiogenesis inhibitor as described herein. A therapeutically effective amount of SEQ ID NO: 1 can vary from minimally activating to highly activating so long as the combination therapy with an angiogenesis inhibitor provides treatment.

In general, dosing parameters of monotherapy with the fusion protein of SEQ ID NO: 1 or any of the combination therapies described herein dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

In addition, an effective dose of the fusion protein of SEQ ID NO: 1 can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The invention provides dosages contained in a "unit dosage form". The phrase "unit dosage form" refers to physically discrete units, each unit containing a predetermined amount of the fusion protein of SEQ ID NO: 1 either alone or in combination with one or more angiogenesis inhibitors (e.g., lenvatinib) and optionally one or more additional therapeutic agents sufficient to produce the desired effect. It will be appreciated that the parameters of a unit dosage form will depend on the particular agent and the effect to be achieved.

Preferably the fusion protein of SEQ ID NO: 1 is administered as a single I.V. infusion per day. A single I.V. infusion may take from 5 minutes to 2 hours. Preferably a therapeutically effective amount of SEQ ID NO: 1 is an amount administered by I.V. infusion to a patient that is encompassed by one or more of the following ranges: from about 0.01 to 1 mg/kg; from about mg/kg to about 0.1 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg or a corresponding fixed dose thereof based on an about 12 to about 50 kg or more child or a 60-70 kg adult.

Preferably, the invention provides pharmaceutical compositions for I.V. administration comprising a dose of the fusion protein of SEQ ID NO: 1 in terms of mg/kg as is often necessary for pediatric patients, for example, the invention provides the fusion protein of SEQ ID NO: 1, at a dose of about 0.1 µg/kg, 0.3 µg/kg, 1 µg/kg, 3 µg/kg, 3.5 µg/kg, 4 µg/kg, 4.5 µg/kg, 5 µg/kg, µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg 14.5 µg/kg or a corresponding fixed dose thereof based on an about 12 to about 50 kg or more child or a 60-70 kg adult.

Preferably the fusion protein of SEQ ID NO: 1 is administered by subcutaneous injection. Preferably, the invention provides pharmaceutical compositions for subcutaneous administration comprising a dose of the fusion protein of SEQ ID NO: 1 of at least about 0.1 mg, 0.2 mg, 0.3 mg, 0.4 mg, 0.5 mg, 0.6 mg, 0.5 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg or 30 mg or a corresponding fixed dose thereof based on an about 12 to about 50 kg or more child or a 60-70 kg adult. The pharmaceutical compositions of the invention may optionally include a pharmaceutically acceptable excipient.

Preferably, the invention provides pharmaceutical compositions for subcutaneous administration comprising a dose of the fusion protein of SEQ ID NO: 1 in terms of µg/kg as is often necessary for pediatric patients, for example, the invention provides the fusion protein of SEQ ID NO: 1, at a dose of about 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 1.5 µg/kg, 2 µg/kg, 2.5 µg/kg, 3 µg/kg, 3.5 µg/kg, 4 µg/kg, 4.5 µg/kg, 5 µg/kg, 5.5 µg/kg, 6 µg/kg, 6.5 µg/kg, 7 µg/kg, 7.5 µg/kg, 8 µg/kg, 8.5 µg/kg, 9 µg/kg, 9.5 µg/kg, 10 µg/kg, 10.5 µg/kg, 11 µg/kg, 11.5 µg/kg, 12 µg/kg, 12.5 µg/kg, 13 µg/kg, 13.5 µg/kg, 14 µg/kg, 14.5 µg/kg, 15 µg/kg or a corresponding fixed dose thereof based on an about 12 to about 50 kg or more child or a 60-70 kg adult.

Preferably an effective amount of SEQ ID NO: 1 that is an amount administered to a patient encompassed by one or more of the following ranges: from about 0.01 to 1 mg/kg; from about 0.01 mg/kg to about 0.1 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

Preferably the dosing regimens of the invention provide subcutaneously administering a pharmaceutical composition comprising the fusion protein of SEQ ID NO: 1 about every 3 days (q3d), about every 4 days (q4d), about every 5 days (q5d), about every 6 days (q6d), about every 7 days (q7d), about every 8 days (q8d), about every 9 days (q9d), about every 10 days Q10d), about every 11 days (gild), about every 12 days (q12d), about every days 13 days (q13d), about every 14 days (q14d), about every 15 days (q15d), about every 16 days (q16d) about every 17 days (q17), about every 18 days (q18d), about every 19 days (q19d), about every 20 days (q20d), about every 21 days, about every 22 days, about every 23 days, about every 24 days, about every days, about every 26 days, about every 27 days, or about every 28 days.

Preferably the fusion protein of SEQ ID NO: 1 is subcutaneously administered in a dose of about 0.1 mg, 1 mg, 3 mg, 6, mg, 10 mg or 30 mg about every 3 days (q3d), about every 4 days (q4d), about every 7 days (q7d), about every 14 days (q14d) or about every 21 days (q21d).

Preferably the dosing regimen for administration of the fusion protein provides for one or more treatment courses. A first course of treatment may take place over a period of days ranging from 1-90 days. Preferably a single treatment course extends for a period of 7 days, 14 days, 21 days, 4 weeks, 6 weeks, 8 weeks, 10 weeks, 12 weeks, 4 months, 5 months, 6 months, 7 months 8 months 9 months, 10 months, 11 months, 12 months or longer. A treatment course may involve, for example, subcutaneous or I.V. administration of the fusion protein of SEQ ID NO: 1 one or more times during the treatment course. There may be one or more consecutive courses of treatment such as a first treatment course followed by a second course of treatment, preferably with period of time such as one day to 1 year between the two courses of treatment.

The actual dose and frequency of administration of the fusion protein of SEQ ID NO: 1 in combination with an angiogenesis inhibitor will vary depend upon the age, weight, and general condition of the subject as well as the severity of the condition being treated, the judgment of the health care professional, and conjugate being administered. The dosing and frequency may also be established based on whether the patient is responsive to one or more of the compounds in the combination. For example, patients may be responsive to the individual agents alone as well as the combination but are more responsive to the combination. By way of further example, patients may be non-responsive to one of the individual agents but are responsive to the combination. By way of still further example, patients may be non-responsive to either of the individual agents alone but are responsive to the combination.

The combination therapy methods described herein include administering at least one angiogenesis inhibitor in combination with the fusion protein of SEQ ID NO: 1. The invention is not limited to any specific angiogenesis inhibitor so long as the molecule inhibits angiogenesis. In some instances, due to, for example, synergistic effects, minimal inhibition of angiogenesis by the molecule may be sufficient in the presence of the fusion protein of SEQ ID NO: 1. Many angiogenesis inhibitors are known in the art, for example, the following is a list of FDA approved angiogenesis inhibitors:

Axitinib (Inlyta®)
Bevacizumab (Avastin®)
Cabozantinib (Cometriq®)
Everolimus (Afinitor®)
Lenalidomide (Revlimid®)
Pazopanib (Votrient®)
Ramucirumab (Cyramza®)
Regorafenib (Stivarga®)
Sorafenib (Nexavar®)
Sunitinib (Sutent®)

Thalidomide (Synovir, Thalomid®)
Vandetanib (Caprelsa®)
Ziv-aflibercept (Zaltrap®).

Given the many commercially available angiogenesis inhibitors and those that are in clinical testing, the skilled person may refer to the literature to obtain information on identifying and testing the activity of any potential angiogenesis inhibitor and also determining suitable dosage and frequency with which to administer the angiogenesis inhibitor alone or in combination with the fusion protein of SEQ ID NO: 1. Preferred angiogenesis inhibitor are those capable of inhibiting more than one RTK and include multiple receptor tyrosine kinase inhibitors.

The amount of angiogenesis inhibitor administered that is sufficient to promote angiogenesis inhibition is referred to herein as an "angiogenesis-inhibitory amount" or dosage range. The skilled person may refer to the scientific literature and package insert of commercially available inhibitors to establish angiogenesis-inhibitory amounts for use in the combination therapy of the invention.

One preferred multiple receptor tyrosine kinase inhibitor is lenvatinib, 4-[3-Chloro-4-(cyclopropylaminocarbonyl) aminophenoxy]-7-methoxy-6-quinolinecarboxamide (CAS #417716-92-8), or a pharmaceutically acceptable salt (such as hydrochloride salt). Lenvatinib is described in further detail in U.S. Pat. No. 7,253,286, incorporated herein by reference. Lenvatinib is represented by Formula I:

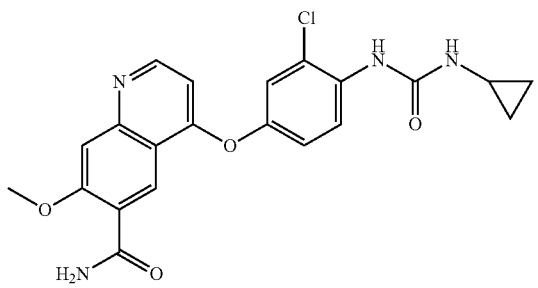

Formula I

Preferably an angiogenesis inhibitory amount of lenvatinib as a daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

Preferably, an angiogenesis inhibitory amount of lenvatinib ranges from about 1 mg to about 30 mg orally on a daily basis, and more preferably about 2 mg to 10 mg orally on a daily basis and more preferably about 5 mg to about 10 mg orally on a daily basis.

Benefits of Combination Treatment Regimens.

The combination therapy of the invention provides many beneficial and unexpected therapeutic effects as evidenced by mice treated with SEQ ID NO: 2, the murine surrogate for SEQ ID NO: 1. Mice treated with combinations of SEQ ID NO: 2 and lenvatinib or an anti-VEGF antibody exhibit durable complete responses to the combination therapy (FIG. 1A and FIG. 2A) and exhibit prolonged survival (FIG. 1B and FIG. 2B). SEQ ID NO: 2 can induce an increase in CD8+ T cells that is amplified by the combination with lenvatinib or an anti-VEGF antibody. Lenvatinib or an anti-VEGF antibody can induce a decrease in macrophages that is amplified by the combination with SEQ ID NO: 2. SEQ ID NO: 2 in combination with lenvatinib or an anti-VEGF antibody can induce an increase in dendritic cells in tumors and spleens of treated mice. Lenvatinib in combination with SEQ ID NO: 2 induced the down regulation of VEGF-induced Esm1 gene expression in tumors resulting in tumor regression in treated mice (FIG. 3). The combination of lenvatinib with SEQ ID NO: 2 resulted in greater cytotoxic gene expression in tumors resulting in tumor regression as well as inhibition of the VEGF pathway in treated mice (FIG. 3).

The analysis of genes associated with T cell signaling suggests that the combination of SEQ ID NO: 2 and lenvatinib results in greater T cell activation in tumors of treated mice. Increases in expression of genes associated with antigen presentation correlates with an increase in dendritic cell infiltration in tumors of mice treated with the combination of SEQ ID NO: 2 and lenvatinib.

Treatment Indications

The combination treatment methods described herein are particularly suitable for the treatment of cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Examples of the solid tumor cancers that may be treated using the combination treatment regimens described herein include, but are not limited to: pancreatic cancer, colorectal cancer, non-small cell lung cancer, renal cell carcinoma; squamous cell carcinoma of the head and neck, bladder cancer, cancers of the prostate, cervix, stomach, endometrium, brain, liver, ovary, testis, head, neck, skin (including melanoma and basal carcinoma), mesothelial lining, esophagus, breast, muscle, connective tissue, lung (including small-cell lung carcinoma and non-small-cell carcinoma), adrenal gland, thyroid, kidney, or bone; glioblastoma, mesothelioma, gastric cancer, sarcoma, choriocarcinoma, cutaneous basocellular carcinoma, and testicular seminoma. In preferred aspects, the cancer is cervical cancer, non-small cell lung cancer, renal cell carcinoma; squamous cell carcinoma of the head and neck, bladder cancer, pancreatic cancer, melanoma, lymphoma or gastric cancer. In more preferred aspects, the cancer is melanoma, non-small cell lung cancer, squamous cell carcinoma of the head and neck, bladder cancer, renal cell carcinoma or gastric carcinoma. The treatment regimens of the invention are particularly suited for treating solid tumors including but not limited to: lymphomas, melanoma, renal cell carcinoma (RCC), advanced solid tumors, tumors that have previously been treated with therapeutic therapy but remain refractory to previous therapies.

Cancers that may also be treated in accordance with invention include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Glioblastoma, Childhood; Glioblastoma, Adult; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm, Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland' Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor, among others.

The combination therapy of the invention are particularly suited for treating solid tumors including but not limited to: lymphomas, melanoma, renal cell carcinoma (RCC), hepatic cell carcinoma (HCC), non-small cell lung cancer (NSCLC), small cell lung cancer (SCLC), squamous cell carcinoma of the head and neck (SCCHN), ovarian cancer, breast cancer and triple negative breast cancer. The combination therapy of the invention is also particularly suited for treatment of advanced solid tumors and tumors that have previously been treated with anti-cancer therapy but remain refractory to previous therapies.

Preferably, the fusion protein of SEQ ID NO: 1 is administered in a combination treatment of cancer by parenteral administration, preferably by subcutaneous injection or intravenous injection and preferably lenvatinib is administered orally. However, other modes of administration of both compounds are also contemplated, such as pulmonary, nasal, buccal, rectal, sublingual and transdermal. As used herein, the term "parenteral" includes subcutaneous, intravenous, intra-arterial, intraperitoneal, intracardiac, intrathecal, and intramuscular injection, as well as infusion injections. Each pharmacological component of the method can be administered separately. Alternatively, if administration of two pharmacological components is desired to be simultaneous—and the two pharmacological components are compatible together and in a given formulation—then the simultaneous administration can be achieved via administration of single dosage form/formulation (e.g., intravenous administration of an intravenous formulation that contains both pharmacologically active agents). One of ordinary skill in the art can determine through routing testing whether two given pharmacological components are compatible together and in a given formulation.

The compositions administered in accordance with the invention may further comprise with a pharmaceutically acceptable diluent, carrier, solubilizer, emulsifier, preservative and/or adjuvant and another pharmaceutical composition comprising one or more therapeutic agents, such as a therapeutic antibody, with a pharmaceutically acceptable diluent, carrier, solubilizer, emulsifier, preservative and/or adjuvant.

The combination treatment methods described herein can continue for as long as the clinician overseeing the patient's care deems the treatment method is effective. Non-limiting parameters that indicate the treatment method is effective include the following: tumor shrinkage (in terms of weight and/or volume); a decrease in the number of individual tumor colonies; tumor elimination; and progression-free survival (PFS).

Exemplary lengths of time associated with the course of combination therapy disclosed herein include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years. Preferably the length of time associated with combination therapy of the invention is up to about 2 years.

Pharmaceutical Compositions

The fusion protein of SEQ ID NO: 1 and angiogenesis inhibitors in accordance with the invention can be in the form of one or more compositions suitable for administration to a subject. In general, such compositions are "pharmaceutical compositions" comprising the fusion protein of SEQ ID NO: 1 and/or an angiogenesis inhibitor(s), and one or more pharmaceutically acceptable or physiologically acceptable diluents, carriers or excipients.

The pharmaceutical compositions of the invention can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of the fusion protein of SEQ ID NO: 1 and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form.

Preferably, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver the pharmaceutical composition, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleaginous suspension. This suspension can be formulated according to the known art using those suitable dispersing or wetting agents and suspending agents mentioned herein. The sterile injectable preparation can also be a sterile injectable solution or suspension in a non-toxic parenterally acceptable diluent or solvent, for example, as a solution in 1,3-butane diol. Acceptable diluents, solvents and dispersion media that can be employed include water, Ringer's solution, isotonic sodium chloride solution, CREMOPHOR EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions can be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrylate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

Suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The pharmaceutical compositions suitable for use in accordance with the invention may be in any format (e.g., sprays for nasal or inhalation use) currently known or developed in the future.

The concentration of a fusion protein of SEQ ID NO: 1 or an angiogenesis inhibitor(s) in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Additional Complementary Combination Therapies

Other anticancer treatment regimens in further combination with the combination therapy of the fusion protein of SEQ ID NO: 1 and an angiogenesis inhibitor(s) are also contemplated for use as further combination therapy for the treatment of cancer. Other therapeutic treatment regimens include other therapeutic immunotherapies such as adoptive cell transfer regimens, antigen-specific vaccination, inhibition of DNA repair proteins (e.g. inhibitors of the nucleic enzyme poly(adenosine 5'-diphospho-ribose) polymerase ["poly(ADP-ribose) polymerase" PARP inhibitors"]) and blockade of immune checkpoint inhibitory molecules, for example cytotoxic T lymphocyte-associated antigen 4 (CTLA-4) and programmed death 1 (PD-1) antibodies.

Treatment regimens with the fusion protein of SEQ ID NO: 1 and an angiogenesis inhibitor in accordance with the invention may also be further combined with other therapeutic agents and/or anti-cancer agents in addition to, or instead of, immune checkpoint inhibitors. Preferably, the therapeutic agent and/or anti-cancer agent is an antibody. Preferably, the therapeutic agent is a therapeutic protein. Preferably, the therapeutic agent is a small molecule. Preferably the anticancer agent is an antigen. Preferably, the therapeutic agent is a population of cells. Preferably, the therapeutic agent is a therapeutic antibody. Preferably the therapeutic agent is another cytotoxic and/or chemotherapeutic agent. The term "cytotoxic agent" as used herein refers to a substance that inhibits or prevents a cellular function and/or causes cell death or destruction. "Chemotherapeutic agent" includes chemical compounds useful in the treatment of cancer. Radiation therapy is another cytotoxic agent.

Immune Checkpoint Inhibitors

Immune checkpoint proteins regulate T cell function in the immune system. T cells play a central role in cell-mediated immunity. Checkpoint proteins interact with specific ligands that send a signal into the T cell and essentially switch off or inhibit T cell function. Cancer cells take advantage of this system by driving high levels of expression of checkpoint proteins on their surface that results in control of the T cells expressing checkpoint proteins on the surface of T cells that enter the tumor microenvironment, thus suppressing the anticancer immune response. As such, inhibition of checkpoint proteins by agents referred to herein as "immune checkpoint protein (ICP) inhibitors" would result in restoration of T cell function and an immune response to the cancer cells. Examples of checkpoint proteins include, but are not limited to: CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, OX40, B-7 family ligands or a combination thereof. Preferably, the immune checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, OX40, A2aR, B-7 family ligands or a combination thereof. Preferably, the checkpoint inhibitor is a biologic therapeutic or a small molecule. Preferably, the checkpoint inhibitor is a monoclonal antibody, a humanized antibody, a fully human antibody, a fusion protein or a combination thereof. Preferably, the PD1 checkpoint inhibitor comprises one or more anti-PD-1 antibodies, including nivolumab and pembrolizumab.

The combination therapy methods described herein include administering at least one checkpoint inhibitor in further combination with the fusion protein of SEQ ID NO: 1 and an angiogenesis inhibitor. The invention is not limited to any specific checkpoint inhibitor so long as the checkpoint inhibitor inhibits one or more activities of the target checkpoint proteins when administered in an effective amount as monotherapy or in combination with the fusion protein of SEQ ID NO: 1. In some instances, due to, for example, synergistic effects, minimal inhibition of the checkpoint protein by the checkpoint inhibitor may be sufficient in the presence of SEQ ID NO: 1. Many checkpoint inhibitors are known in the art, for example, the following is a list of FDA approved checkpoint protein inhibitors:

ipilimumab (YERVOY®)
pembrolizumab (KEYTRUDA®)
atezolizumab (TECENTRIQ®)
durvalumab (IMFINZ®)
avelumab (BAVENCIO®)
nivolumab (OPDIVO®).

A preferred treatment regimen of the invention combines the fusion protein of SEQ ID NO: 1 administered in accordance with the invention with the checkpoint inhibitor, pembrolizumab. Preferably, pembrolizumab is administered on the first day of each treatment cycle of the treatment regimen according to the invention. Preferably 200 mg of pembrolizumab is administered in accordance with manufacturer's recommendations, generally once every three weeks or 21 days.

Antibodies

Preferably the administration of SEQ ID NO: 1 in combination with an angiogenesis inhibitor may be further combined with a therapeutic antibody. Methods of producing antibodies, and antigen-binding fragments thereof, are well known in the art and are disclosed in, e.g., U.S. Pat. No. 7,247,301, US2008/0138336, and U.S. Pat. No. 7,923,221, all of which are herein incorporated by reference in their entirety. Therapeutic antibodies that can be used in the methods of the present invention include, but are not limited to, any of the art-recognized therapeutic antibodies that are approved for use, in clinical trials, or in development for clinical use. In some embodiments, more than one therapeutic antibody can be included in the combination therapy of the present invention.

Non-limiting examples of therapeutic antibodies include the following, without limitation:

trastuzumab (HERCEPTIN™. by Genentech, South San Francisco, Calif.), which is used to treat HER-2/neu positive breast cancer or metastatic breast cancer;
bevacizumab (AVASTIN™ by Genentech), which is used to treat colorectal cancer, metastatic colorectal cancer, breast cancer, metastatic breast cancer, non-small cell lung cancer, or renal cell carcinoma;

rituximab (RITUXAN™ by Genentech), which is used to treat non-Hodgkin's lymphoma or chronic lymphocytic leukemia;

pertuzumab (OMNITARG™ by Genentech), which is used to treat breast cancer, prostate cancer, non-small cell lung cancer, or ovarian cancer;

cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer;

IMC-1C11 (ImClone Systems Incorporated), which is used to treat colorectal cancer, head and neck cancer, as well as other potential cancer targets;

tositumomab and tositumomab and iodine $I^{131}$ (BEXXAR™ by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy;

$In^{111}$ ibritumomab tiuxetan; $Y^{90}$ ibritumomab tiuxetan; $I^{111}$ ibritumomab tiuxetan and $Y^{90}$ ibritumomab tiuxetan (ZEVALIN™ by Biogen Idec, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma;

EMD 7200 (EMD Pharmaceuticals, Durham, N.C.), which is used for treating for treating non-small cell lung cancer or cervical cancer;

SGN-30 (a genetically engineered monoclonal antibody targeted to CD30 antigen by Seattle Genetics, Bothell, Wash.), which is used for treating Hodgkin's lymphoma or non-Hodgkin's lymphoma;

SGN-15 (a genetically engineered monoclonal antibody targeted to a Lewis γ-related antigen that is conjugated to doxorubicin by Seattle Genetics), which is used for treating non-small cell lung cancer;

SGN-33 (a humanized antibody targeted to CD33 antigen by Seattle Genetics), which is used for treating acute myeloid leukemia (AML) and myelodysplastic syndromes (MDS);

SGN-40 (a humanized monoclonal antibody targeted to CD40 antigen by Seattle Genetics), which is used for treating multiple myeloma or non-Hodgkin's lymphoma;

SGN-35 (a genetically engineered monoclonal antibody targeted to a CD30 antigen that is conjugated to auristatin E by Seattle Genetics), which is used for treating non-Hodgkin's lymphoma;

SGN-70 (a humanized antibody targeted to CD70 antigen by Seattle Genetics), that is used for treating renal cancer and nasopharyngeal carcinoma;

SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

The therapeutic antibodies to be used in the methods of the present invention are not limited to those described herein. For example, the following approved therapeutic antibodies can also be used in the methods of the invention: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chronic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies for use in accordance with the invention can also target molecules expressed by immune cells, such as, but not limited to, tremelimumab (CP-675,206) and ipilimumab (MDX-010) which targets CTLA4 and has the effect of tumor rejection, protection from re-challenge, and enhanced tumor-specific T cell responses; OX86 which targets OX40 and increases antigen-specific CD8+ T cells at tumor sites and enhances tumor rejection; CT-011 which targets PD 1 and has the effect of maintaining and expanding tumor specific memory T cells and activates NK cells; BMS-663513 which targets CD137 and causes regression of established tumors, as well as the expansion and maintenance of CD8+ T cells, and daclizumab (ZENAPAX™) which targets CD25 and causes transient depletion of CD4+ CD25+FOXP3+Tregs and enhances tumor regression and increases the number of effector T cells. A more detailed discussion of these antibodies can be found in, e.g., Weiner et al., Nature Rev. Immunol 2010; 10:317-27.

Preferably, the antibody is a pro-inflammatory and/or pro-tumorigenic cytokine targeting antibody including, but not limited to, anti-TNF antibodies, anti-IL-1Ra receptor targeting antibodies, anti-IL-1 antibodies, anti-IL-6 receptor antibodies, and anti-IL-6 antibodies. Preferably antibodies include those that target pro-inflammatory T helper type 17 cells (TH17). The therapeutic antibody can be a fragment of an antibody; a complex comprising an antibody; or a conjugate comprising an antibody. The antibody can optionally be chimeric or humanized or fully human.

Therapeutic Proteins and Polypeptides

Preferably the methods of the invention include administration of the fusion protein of SEQ ID NO: 1 and an angiogenesis inhibitor in accordance with the treatment regimen of the invention, in further combination with a therapeutic protein or peptide. Therapeutic proteins that are effective in treating cancer are well known in the art, Preferably, the therapeutic polypeptide or protein is a "suicide protein" that causes cell death by itself or in the presence of other compounds.

A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, beta-glucuronidase, penicillin-V-amidase, penicillin-G-amidase, beta-lactamase, nitroreductase, carboxypeptidase A, linamarase (also referred to as β-glucosidase), the E. coli gpt gene, and the E. coli Deo gene, although others are known in the art. In some embodiments, the suicide protein converts a prodrug into a toxic compound.

As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-(3-D-arabinofuranosyl)-5-iodouracil) for thymidine kinase; ifosfamide for oxidoreductase; 6-methoxypurine arabinoside for VZV-TK; 5-fluorocytosine for cytosine deaminase; doxorubicin for beta-glucuronidase; CB 1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug.

Preferably the therapeutic protein or polypeptide, is a cancer suppressor, for example p53 or Rb, or a nude acid encoding such a protein or polypeptide. Those of skill know of a wide variety of such cancer suppressors and how to obtain them and/or the nucleic acids encoding them.

Other examples of anti-cancer/therapeutic proteins or polypeptides include pro-apoptotic therapeutic proteins and polypeptides, for example, p15, p16, or $p21^{WAF-1}$.

Cytokines, and nucleic acid encoding them may also be used as therapeutic proteins and polypeptides. Examples include: GM-CSF (granulocyte macrophage colony stimulating factor); TNF-alpha (Tumor necrosis factor alpha); Interferons including, but not limited to, IFN-alpha and IFN-gamma; and Interleukins including, but not limited to, Interleukin-1 (IL-1), Interleukin-Beta (IL-beta), Interleukin-2 (IL-2), Interleukin-4 (IL-4), Interleukin-5 (IL-5), Interleukin-6 (IL-6), Interleukin-7 (IL-7), Interleukin-8 (IL-8), Interleukin-10 (IL-10), Interleukin-12 (IL-12), Interleukin-13 (IL-13), Interleukin-14 (IL-14), Interleukin-15 (IL-15), Interleukin-16 (IL-16), Interleukin-18 (IL-18), Interleukin-23 (IL-23), Interleukin-24 (IL-24), although other embodiments are known in the art.

Additional examples of cytocidal genes includes, but is not limited to, mutated cyclin G1 genes. By way of example, the cytocidal gene may be a dominant negative mutation of the cyclin G1 protein (e.g., WO/01/64870).

Vaccines

Preferably, the therapeutic regimens of the invention include administration of a fusion protein of SEQ ID NO: 1 in combination with an angiogenesis inhibitor in further combination with administration of a cancer vaccine for stimulating a cancer specific-immune response, e.g., innate and adaptive immune responses, for generating host immunity against a cancer. Illustrative vaccines include, but are not limited to, for example, antigen vaccines, whole cell vaccines, dendritic cell vaccines, and DNA vaccines. Depending upon the particular type of vaccine, the vaccine composition may include one or more suitable adjuvants known to enhance a subject's immune response to the vaccine.

The vaccine may, for example, be cellular based, i.e., created using cells from the patient's own cancer cells to identify and obtain an antigen. Exemplary vaccines include tumor cell-based and dendritic-cell based vaccines, where activated immune cells from the subject are delivered back to the same subject, along with other proteins, to further facilitate immune activation of these tumor antigen primed immune cells. Tumor cell-based vaccines include whole tumor cells and gene-modified tumor cells. Whole tumor cell vaccines may optionally be processed to enhance antigen presentation, e.g., by irradiation of either the tumor cells or tumor lysates). Vaccine administration may also be accompanied by adjuvants such as bacillus calmette-guerin (BCG) or keyhole limpet hemocyanin (KLH), depending upon the type of vaccine employed. Plasmid DNA vaccines may also be used and can be administered via direct injection or biolistically. Also contemplated for use are peptide vaccines, viral gene transfer vector vaccines, and antigen-modified dendritic cells (DCs).

Preferably the vaccine is a therapeutic cancer peptide-based vaccine. Peptide vaccines can be created using known sequences or from isolated antigens from a subject's own tumor(s) and include neoantigens and modified antigens. Illustrative antigen-based vaccines include those where the antigen is a tumor-specific antigen. For example, the tumor-specific antigen may be selected from a cancer-testis antigen, a differentiation antigen, and a widely occurring over-expressed tumor associated antigen, among others. Recombinant peptide vaccines, based on peptides from tumor-associated antigens, when used in the instant method, may be administered or formulated with, an adjuvant or immune modulator. Illustrative antigens for use in a peptide-based vaccine include, but are not limited to, the following, since this list is meant to be purely illustrative. For example, a peptide vaccine may comprise a cancer-testis antigen such as MAGE, BAGE, NY-ESO-1 and SSX-2, encoded by genes that are normally silenced in adult tissues but transcriptionally reactivated in tumor cells. Alternatively, the peptide vaccine may comprise a tissue differentiation associated antigen, i.e., an antigen of normal tissue origin and shared by both normal and tumorous tissue. For example, the vaccine may comprise a melanoma-associated antigen such as gp100, Melan-A/Mart-1, MAGE-3, or tyrosinase; or may comprise a prostate cancer antigen such as PSA or PAP. The vaccine may comprise a breast cancer-associated antigen such as mammaglobin-A. Other tumor antigens that may be comprised in a vaccine for use in the instant method include, for example, CEA, MUC-1, HER1/Nue, hTERT, ras, and B-raf. Other suitable antigens that may be used in a vaccine include SOX-2 and OCT-4, associated with cancer stem cells or the EMT process.

Antigen vaccines include multi-antigen and single antigen vaccines. Exemplary cancer antigens may include peptides having from about 5 to about 30 amino acids, or from about 6 to amino acids, or from about 8 to 20 amino acids.

As described above, an immunostimulatory adjuvant (different from RSLAIL-2) may be used in a vaccine, in particular, a tumor-associated antigen-based vaccine, to assist in generating an effective immune response. For example, a vaccine may incorporate a pathogen-associated molecular pattern (PAMP) to assist in improving immunity. Additional suitable adjuvants include monophosphoryl lipid A, or other lipopolysaccharides; toll-like receptor (TLR) agonists such as, for example, imiquimod, resiquimod (R-848), TLR3, IMO-8400, and rintatolimod. Additional adjuvants suitable for use include heat shock proteins.

A genetic vaccine typically uses viral or plasmid DNA vectors carrying expression cassettes. Upon administration, they transfect somatic cells or dendritic cells as part of the inflammatory response to thereby result in cross-priming or direct antigen presentation. Preferably, a genetic vaccine is one that provides delivery of multiple antigens in one immunization. Genetic vaccines include DNA vaccines, RNA vaccines and viral-based vaccines. DNA vaccines for use in the instant methods are bacterial plasmids that are constructed to deliver and express tumor antigen. DNA vaccines may be administered by any suitable mode of administration, e.g., subcutaneous or intradermal injection, but may also be injected directly into the lymph nodes.

Additional modes of delivery include, for example, gene gun, electroporation, ultrasound, laser, liposomes, microparticles and nanoparticles.

Preferably, the vaccine comprises a neoantigen, or multiple neoantigens. Preferably, the vaccine is a neoantigen-based vaccine. Preferably a neoantigen-based vaccine (NBV) composition may encode multiple cancer neoantigens in tandem, where each neoantigen is a polypeptide fragment derived from a protein mutated in cancer cells. For instance, a neoantigenic vaccine may comprise a first vector comprising a nucleic acid construct encoding multiple immunogenic polypeptide fragments, each of a protein mutated in cancer cells, where each immunogenic polypeptide fragment comprises one or more mutated amino acids flanked by a variable number of wild type amino acids from the original protein, and each polypeptide fragment is joined head-to-tail to form an immunogenic polypeptide. The lengths of each of the immunogenic polypeptide fragments forming the immunogenic polypeptide can vary.

Viral gene transfer vector vaccines may also be used; in such vaccines, recombinant engineered virus, yeast, bacteria or the like is used to introduce cancer-specific proteins to the patient's immune cells. In a vector-based approach, which can be tumor lytic or non-tumor lytic, the vector can increase the efficiency of the vaccine due to, for example, its inherent immunostimulatory properties. Illustrative viral-based vectors include those from the poxviridae family, such as vaccinia, modified vaccinia strain Ankara and avipoxviruses. Also suitable for use is the cancer vaccine, PROST-VAC, containing a replication-competent vaccinia priming vector and a replication-incompetent fowlbox-boosting vector. Each vector contains transgenes for PSA and three co-stimulatory molecules, CD80, CD54 and CD58, collectively referred to as TRICOM. Other suitable vector-based cancer vaccines include Trovax and TG4010 (encoding MUC1 antigen and IL-2). Additional vaccines for use include bacteria and yeast-based vaccines such as recombinant *Listeria monocytogenes* and *Saccharomyces cerevisae*.

The foregoing vaccines may be combined and/or formulated with adjuvants and other immune boosters to increase efficacy. Depending upon the particular vaccine, administration may be either intratumoral or non-intratumoral (i.e., systemic).

Small Molecules

Preferably, the therapeutic regimens of the invention include administration of a fusion protein of SEQ ID NO: 1 in combination with an angiogenesis inhibitor in further combination with administration of an anticancer small molecule. Small molecules that are effective in treating cancer are well known in the art and include antagonists of factors that are involved in tumor growth, such as EGFR, ErbB2 (also known as Her2) ErbB3, ErbB4, or TNF. Non-limiting examples include small molecule receptor tyrosine kinase inhibitors (RTKIs) that target one or more tyrosine kinase receptors, such as VEGF receptors, FGF receptors, EGF receptors and PDGF receptors.

Many therapeutic small molecule RTKIs are known in the art, including, but are not limited to, vatalanib (PTK787), erlotinib (TARCEVA™), OSI-7904, ZD6474 (ZACTIMA™), ZD6126 (ANG453), ZD1839, sunitinib (SUTENT™), semaxanib (SU5416), AMG706, AG013736, Imatinib (GLEEVEC™), MLN-518, CEP-701, PKC-412, Lapatinib (GSK572016), VELCADE™, AZD2171, sorafenib (NEXAVAR™), XL880, and CHIR-265. Small molecule protein tyrosine phosphatase inhibitors, such as those disclosed in Jiang et al., *Cancer Metastasis Rev.* 2008; 27:263-72 are also useful for practicing the methods of the invention. Such inhibitors can target, e.g., HSP2, PRL, PTP1B, or Cdc25 phosphatases.

Small molecules that target Bcl-2/Bcl-XL, such as those disclosed in US2008/0058322, are also useful for practicing the methods of the present invention. Further exemplary small molecules for use in the present invention are disclosed in Zhang et al. Nature Reviews: Cancer 2009; 9:28-39. In particular, chemotherapeutic agents that lead to immunogenic cell death such as anthracycline (Kepp et al., *Cancer and Metastasis Reviews* 2011; 30:61-9) will be well suited for synergistic effects with extended-PK IL-2.

Cancer Antigens

Preferably, the therapeutic regimens of the invention include administration of a fusion protein of SEQ ID NO: 1 in combination with an angiogenesis inhibitor in further combination with a cancer antigen, e.g., for use as a cancer vaccine (see, e.g., Overwijk, et al., Journal of Experimental Medicine 2008; 198:569-80). Other cancer antigens that can be used in vaccinations include, but are not limited to, (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen.

In another embodiment, the cancer antigen is a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen. The described cancer antigens are only exemplary, and that any cancer antigen can be targeted in the present invention.

Preferably, the cancer antigen is a mucin-1 protein or peptide (MUC-1) that is found on all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In another embodiment, the cancer antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5):1595-1599).

Preferably, the cancer antigen is a human epidermal growth factor receptor-2 (HER-2/neu) antigen. Cancers that have cells that overexpress HER-2/neu are referred to as HER-2/neu$^-$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK™ Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™ Accession No. AAA58637. Based on these sequences, one skilled in the art could develop HER-2/neu antigens using known assays to find appropriate epitopes that generate an effective immune response.

Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [$9_{754}$]; and the like.

Preferably, the cancer antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR cancers. Exemplary EGFR cancers include lung cancer, head and neck cancer, colon cancer, colorectal cancer, breast cancer, prostate cancer, gastric cancer, ovarian cancer, brain cancer and bladder cancer.

Preferably, the cancer antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

Preferably, the cancer antigen is prostate-specific antigen (PSA) and/or prostate-specific membrane antigen (PSMA) that are prevalently expressed in androgen-independent prostate cancers.

Preferably, the cancer antigen is Gp-100 Glycoprotein 100 (gp 100) is a tumor-specific antigen associated with melanoma.

Preferably, the cancer antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

Preferably, the cancer antigen is carbohydrate antigen 10.9 (CA 19.9). CA 19.9 is an oligosaccharide related to the Lewis A blood group substance and is associated with colorectal cancers.

Preferably, the cancer antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Mel an A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

Preferably, the cancer antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine for leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In another embodiment of the invention, the cancer antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

The cancer antigen can be a cell, a protein, a peptide, a fusion protein, DNA encoding a peptide or protein, RNA encoding a peptide or protein, a glycoprotein, a lipoprotein, a phosphoprotein, a carbohydrate, a lipopolysaccharide, a lipid, a chemically linked combination of two or more thereof, a fusion or two or more thereof, or a mixture of two or more thereof, or a virus encoding two or more thereof, or an oncolytic virus encoding two or more thereof. In another embodiment, the cancer antigen is a peptide comprising about 6 to about 24 amino acids; from about 8 to about 20 amino acids; from about 8 to about 12 amino acids; from about 8 to about 10 amino acids; or from about 12 to about 20 amino acids. In one embodiment, the cancer antigen is a peptide having a MHC Class I binding motif or a MHC Class II binding motif. In another embodiment, the cancer antigen comprises a peptide that corresponds to one or more cytotoxic T lymphocyte (CTL) epitopes.

Cell Therapy

Preferably, the therapeutic regimens of the invention include administration of a fusion protein of SEQ ID NO: 1 in combination with an angiogenesis inhibitor in further combination with a therapeutic cell therapy. Cell therapies that are useful for treating cancer are well known and are disclosed in, e.g., U.S. Pat. No. 7,402,431. In a preferred embodiment, the cell therapy is T cell transplant. In a preferred method, T cells are expanded ex vivo with IL-2 prior to transplantation into a subject. Methods for cell therapies are disclosed in, e.g., U.S. Pat. No. 7,402,431, US2006/0057121, U.S. Pat. Nos. 5,126,132, 6,255,073 5,846,827, 6,251,385, 6,194,207, 5,443,983, 6,040,177, 5,766,920, and US2008/0279836.

Other Cytotoxic and Chemotherapeutic Agents

Preferably, the therapeutic regimens of the invention include administration of a fusion protein of SEQ ID NO: 1 in combination with an angiogenesis inhibitor in further combination with one or more chemotherapeutic agents including but not limited to, alkylating agents, antitumor antibiotics, antimetabolic agents, other anti-tumor antibiotics, and plant derived agents.

Alkylating agents are drugs which impair cell function by forming covalent bonds with amino, carboxyl, sulfhydryl and phosphate groups in biologically important molecules. The most important sites of alkylation are DNA, RNA and proteins. Alkylating agents depend on cell proliferation for activity but are not cell-cycle-phase-specific. Alkylating agents suitable for use in the present invention include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitroso-ureas (e. g. BCNU, carmustine, lomustine, streptozocin), nonclassic alkylating agents (e.g., altretamine, dacarbazine, and procarbazine), and platinum compounds (e.g., carboplastin, oxaliplatin and cisplatin).

Antitumor antibiotics like adriamycin intercalate DNA at guanine-cytosine and guanine-thymine sequences, resulting in spontaneous oxidation and formation of free oxygen radicals that cause strand breakage. Other antibiotic agents suitable for use in the present invention include, but are not limited to, anthracyclines (e. g. doxorubicin, daunorubicin, epirubicin, idarubicin and anthracenedione), mitomycin C, bleomycin, dactinomycin, and plicatomycin.

Antimetabolic agents suitable for use in the present invention include but are not limited to, floxuridine, fluorouracil, methotrexate, leucovorin, hydroxyurea, thioguanine, mercaptopurine, cytarabine, pentostatin, fludarabine phosphate, cladribine, asparaginase, and gemcitabine.

Plant derived agents include taxanes, which are semisynthetic derivatives of extracted precursors from the needles of yew plants. These drugs have a novel 14-member ring, the taxane. Unlike the vinca alkaloids, which cause microtubular disassembly, the taxanes (e.g., taxol) promote microtubular assembly and stability, therefore blocking the cell cycle in mitosis. Other plant derived agents include, but are not limited to, vincristine, vinblastine, vindesine, vinzolidine, vinorelbine, etoposide, teniposide, and docetaxel.

Radiation Therapy

Preferably, the therapeutic regimens of the invention include administration of a fusion protein of SEQ ID NO: 1 in combination with an angiogenesis inhibitor in further combination with radiation therapy. The term "radiation therapy" may be used interchangeably with the term "radiotherapy", is a type of cancer treatment that uses beams of intense energy to kill cancer cells. Radiation therapy most often uses X-rays, but gamma rays, electron beams, or protons also can be used. The term "radiation therapy" most often refers to external beam radiation therapy. During this type of radiation, the high-energy beams come from a machine outside of the patient's body that aims the beams at a precise point on the body. Each session is quick and painless, lasting about 15 minutes. As used herein, the term "session" or "session of treatment" refers to each radiotherapy treatment. A radiation therapy "regimen" or "sched-ule" usually consists of a specific number of treatments given over a set period of time, depending on the type and the stage of the cancer.

Recombinant Production

Preferably the fusion protein of SEQ ID NO: 1 is produced using recombinant techniques. The fusion protein can be produced as an intracellular protein or as a secreted protein, using any suitable construct and any suitable host cell, which can be a prokaryotic or eukaryotic cell, such as a bacterial (e.g., E. coli) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al., (1995) Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences and can provide for inducible or constitutive expression where the coding region is operably linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The fusion protein of SEQ ID NO: 1 can be prepared in substantially pure or isolated form (e.g., free from other polypeptides). The polypeptides can be present in a composition that is enriched for the polypeptide relative to other components that can be present (e.g., other polypeptides or other host cell components). For example, purified fusion protein can be provided such that the fusion protein is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

Preferably, the fusion protein of SEQ ID NO: 1 may be produced using a biological recombinant expression system typically involving transfecting cells with a DNA vector that contains a genetic template encoding the fusion protein of SEQ ID NO: 1 and then culturing the cells so that they transcribe and translate the Fusion Protein. Typically, the cells are then lysed to extract the expressed protein for subsequent purification. Both prokaryotic and eukaryotic in vivo protein expression systems are suitable for use. Preferably, the fusion protein of SEQ ID NO: 1 is produced in CHO cells.

Kits

Also provided are kits comprising a fusion protein of SEQ ID NO: 1 formulated for administration, and optionally any other chemotherapeutic or anti-cancer agent. The kits are generally in the form of a physical structure housing various components, as described below, and can be utilized, for example, in practicing the methods described above. A kit can include the fusion protein of SEQ ID NO: 1 (provided in, e.g., a sterile container), which can be in the form of a pharmaceutical composition suitable for administration to a subject.

The pharmaceutical composition can be provided in a form that is ready for use or in a form requiring, for example, reconstitution or dilution prior to administration. When the compositions are in a form that needs to be reconstituted by a user, the kit can also include buffers, pharmaceutically acceptable excipients, and the like, packaged with or separately from the fusion protein of SEQ ID NO: 1. When combination therapy (e.g., the fusion protein of SEQ ID NO: 1 and an immune checkpoint inhibitor(s) is contemplated, the kit can contain the several agents separately or they can already be combined in the kit. Similarly, when additional complementary therapy is required (e.g., a fusion protein of SEQ ID NO: 1, an immune checkpoint inhibitor(s), and an additional complementary therapy or agent), the kit can contain the several agents separately or two or more of them can already be combined in the kit.

A kit of the invention can be designed for conditions necessary to properly maintain the components housed therein (e.g., refrigeration or freezing). A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.).

Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXAMPLES

The following examples are offered by way of illustration and are not to be construed as limiting the invention as claimed in any way.

Example 1—Lenvatinib in Combination with SEQ ID NO: 2

Objectives:

Evaluating the anti-tumor efficacy of lenvatinib, the fusion protein of SEQ ID NO: 2 (the mouse ortholog construct of the fusion protein of SEQ ID NO: 1), and a combination of the two agents in syngeneic mouse models of cancer (mouse colon cancer cell line, MC38 in female C57BL/6 mice).

Design of SEQ ID NO: 2:

Murine IL-2 and IL2Ra sequences were obtained (UniProtKB-P04351 and P01590 respectively) and sequence alignments of the mouse sequences and human sequences (UnitProtKB P60568 and P01589) and were used to map the mouse sequences to the circularly permuted human IL-2 sequence of SEQ ID NO: 1.

The resulting mouse ortholog of SEQ ID NO: 2 has the following amino acid sequence:

(SEQ ID NO: 2)
SKSFQLEDAENFISNIRVTVVKLKGSDNTFECQFDDESATVVDFLRRWI

AFCQSIISTSPQGGSSSTQQQQQHLEQLLMDLQELLSRMENYRNLKLPR

MLTFKFYLPKQATELKDLQCLEDELGPLRHVLDLTQGSGGGSELCLYDP

PEVPNATFKALSYKNGTILNCECKRGFRRLKELVYMRCLGNSWSSNCQC

TSNSHDKSRKQVTAQLEHQKEQQTTTDMQKPTQSMHQENLTGHCREPPP

WKHEDSKRIYHFVEGQSVHYECIPGYKALQRGPAISICKMKCGKTGWTQ

PQLTCVDGSHHHHHH.

The His-tag at the C-terminal end of SEQ ID NO: 2 is used for purification and may be present in the expressed protein or optionally may be removed. The construct used to recombinantly produce the protein may optionally include a signal peptide, for example, a signal peptide having the following amino acid sequence: MYRMQLLSCIALSLALVTNS (SEQ ID NO: 3).

Experimental Design:

The studies will determine if the combination treatment can enhance the efficacy of the monotherapies. These studies include multiple doses of the two agents to define the optimal dose of the combination. Standard readouts will include tumor growth inhibition and survival. Animal models used for this study include MC38 in order to discern if combination with SEQ ID NO: 2 in mouse models will help to augment the sensitivity to lenvatinib.

The characteristics of each animal study group, the administration of the test articles and timing, the collection of samples and the overall study design are as shown in Tables 1 and 2:

TABLE 1

| Group | n | Treatment Regimen 1 ||||  Treatment Regimen 2 ||||
|---|---|---|---|---|---|---|---|---|---|
| | | Agent | mg/kg | Route | Schedule | Agent | mg/kg | Route | Schedule |
| 1 | 10 | vehicle 1 | — | sc | days 1, 4, 7, 10, 13, 16, 19 | vehicle 2 | — | po | qd × 28 |
| 2 | 10 | vehicle 1 | — | sc | days 1, 4, 7, 10, 13, 16, 19 | Lenvatinib | 10 | po | qd × 28 |
| 3 | 10 | vehicle 1 | — | sc | days 1, 4, 7, 10, 13, 16, 19 | Lenvatinib | 30 | po | qd × 28 |
| 4 | 10 | vehicle 1 | — | sc | days 1, 4, 7, 10, 13, 16, 19 | Lenvatinib | 100 | po | qd × 28 |
| 5 | 10 | SEQ ID NO: 2 | 3 | sc | days 1, 4, 7, 10, 13, 16, 19 | vehicle 2 | — | po | qd × 28 |
| 6 | 10 | SEQ ID NO: 2 | 3 | sc | days 1, 4, 7, 10, 13, 16, 19 | Lenvatinib | 10 | po | qd × 28 |

TABLE 2

| Group | n | Treatment Regimine ||||  Median |||
|---|---|---|---|---|---|---|---|---|
| | | Agent | mg/kg | Route | Schedule | TTE | T − C | % TGD |
| 1 | 9 | vehicle 1 | — | sc | days 1, 4, 7, 10, 13, 16, 19 | 14.3 | — | — |
| | | vehicle 2 | — | po | qd × 28 | | | |
| 2 | 8 | vehicle 1 | — | sc | days 1, 4, 7, 10, 13, 16, 19 | 38.3 | 24.0 | 168 |
| | | Lenvatinib | 10 | po | qd × 28 | | | |
| 3 | 9 | vehicle 1 | — | sc | days 1, 4, 7, 10, 13, 16, 19 | 37.4 | 23.1 | 162 |
| | | Lenvatinib | 30 | po | qd × 28 | | | |
| 4 | 9 | vehicle 1 | — | sc | days 1, 4, 7, 10, 13, 16, 19 | 37.7 | 23.4 | 164 |
| | | Lenvatinib | 100 | po | qd × 28 | | | |
| 5 | 9 | SEQ ID NO: 2 | 3 | sc | days 1, 4, 7, 10, 13, 16, 19 | 16.4 | 2.1 | 15 |
| | | vehicle 2 | — | po | qd × 28 | | | |
| 6 | 7 | SEQ ID NO: 2 | 3 | sc | days 1, 4, 7, 10, 13, 16, 19 | 51.0 | 36.7 | 257 |
| | | Lenvatinib | 10 | po | qd × 28 | | | |

| | Statistical Significance || MTV (n) | Regressions ||| Mean BW | Deaths ||
|---|---|---|---|---|---|---|---|---|---|
| Group | vs G1 | vs G6 | Day 53 | PR | CR | TFS | Nadir | TR | NTRu |
| 1 | — | *** | — | 0 | 0 | 0 | — | 0 | 1 |
| 2 | *** | *** | — | 1 | 0 | 0 | — | 0 | 2 |
| 3 | *** | — | — | 0 | 0 | 0 | — | 0 | 1 |
| 4 | *** | — | — | 0 | 0 | 0 | — | 0 | 1 |
| 5 | * | *** | — | 0 | 0 | 0 | — | 0 | 1 |
| 6 | *** | — | 4 (3) | 2 | 3 | 3 | −2.8% Day 6 | 0 | 3 |

Table 2 displays the scheduled treatment regimen at completion of the study.
vehicle 1 = PBS
vehicle 2 = 0.5% Methylcellulose:0.5% Tween 20 in saline
Study Endpoint = 1000 mm$^3$;
Study Duration = 53 Days
n = number of animals in a group not dead from accidental or unknown causes, or euthanized for sampling
TTE = time to endpoint,
T − C = difference between median TTE (days) of treated versus control group, % TGD = [(T − C)/C] × 100
The maximum T − C in this study is 38.7 days (271%), compared to Group 1
Statistical Significance (Logrank test):
ne = not evaluable,
ns = not significant,
* = P < 0.05,
** = P < 0.07,
*** = P < 0.001, compared to Group 1 or group indicated
MTV (n) = median tumor volume (mm3) for the number of animals on the Day of TGD analysis (excludes animals with tumor volume at endpoint)
PR = partial regressions;
CR = total number complete regressions;
TFS = tumor free survivors, i.e., tumor volume ≤ 13.5 mm3 for the final three measurements of the study
Mean BW Nadir = lowest group mean body weight, as % change from Day 1;
— indicates no decrease in mean body weight was observed
TR = treatment-related death;
NTRu = non-treatment-related death due to unknown etiology Mice Female C57BL/6 mice (C57BL/6 N Crl Charles River) were nine weeks old on Day 1 of the study and had a body weight (BW) range of 17.8 to 26.7 g. Animals were fed ad libitum water (reverse osmosis, 1 ppm Cl) and NIH 31 Modified and Irradiated Lab Diet ° consisting of 18.0% crude protein, 5.0% crude fat, and 5.0% crude fiber. Mice also received Diet Gel supplements upon arrival and throughout the study. The mice were housed on irradiated Enrich-o'Cobs™ bedding in static microisolators on a 12-hour light cycle at 20-22° C. (68-72° F.) and humidity. Charles River Discovery Services North Carolina (CR Discovery Services) specifically complies with the recommendations of the *Guide for Care and Use of Laboratory Animals* with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumor Cell Culture

MC38 murine colon carcinoma cells were grown to mid-log phase in DMEM medium containing 10% fetal bovine serum, 2 mM glutamine, 100 units/mL, penicillin G, 100 μg/mL streptomycin sulfate and 25 μg/mL gentamicin. The tumor cells were cultured in tissue culture flasks in a humidified incubator at 37° C., in an atmosphere of 5% CO2 and 95% air.

In Vivo Implantation

On the day of implant, MC38 cells were harvested during log phase growth and re-suspended in phosphate buffered saline (PBS) at a concentration of $5 \times 10^6$ cells/mL. Mice were anesthetized with isoflurane and tumors were initiated by subcutaneously implanting $5 \times 10^5$ MC38 cells (in a 0.1 mL suspension) into the right flank of each test animal. Tumors were monitored as their volumes approached the target range of 80 to 120 mm$^3$. Tumors were measured in two dimensions using calipers, and volume was calculated using the formula:

$$\text{Tumor Volume (mm}^3\text{)} = \frac{w^2 \times l}{2}$$

where w=width and l=length, in mm, of the tumor. Tumor weight may be estimated with the assumption that 1 mg is equivalent to 1 mm$^3$ of tumor volume. Fourteen days after tumor implantation, designated as Day 1 of the study, the animals were sorted into thirteen groups (Groups 1-12 n=10, Group 13 n=5) with individual tumor volumes ranging from 75 to 144 mm$^3$ and group mean tumor volumes ranging from 102 to 104 mm$^3$.

Therapeutic Agents

Lenvatinib was stored at ambient temperature protected from the light and SEQ ID NO: 2 was stored as a 3.03 mg/mL stock solution at −80° C. protected from the light. Every week, lenvatinib was formulated in vehicle 2 (0.5% methylcellulose (MC) and 0.5% polysorbate-20 in saline in deionized (DI) water) to obtain a 10 mg/mL clear colorless dosing solution which delivered 100 mg/kg when administered in a dosing volume of 10 mL/kg (0.2 mL/20 g mouse) adjusted to the body weight of each animal. Additional aliquots of the 10 mg/mL solution were further diluted with vehicle 2 to concentrations of 3 and 1 mg/mL which provided dosages of 30 and 10 mg/kg, respectively, when administered in a dosing volume of 10 mL/kg. Dosing solutions were protected from light and stirred continuously at room temperature before and during dosing.

SEQ ID NO: 2 stock solution was thawed and aliquoted for use during the week. On each day of dosing aliquots were diluted in Vehicle 1 (sterile PBS, pH 7.4) and held at 4° C. protected from the light until dosing to obtain dosing solutions 0.3 mg/mL, which delivered 3 mg/kg when administered in a dosing volume of 10 mL/kg adjusted to the body weight of each animal.

Treatment

On Day 1 of the study, mice bearing established subcutaneous MC38 tumors were sorted into six groups (n=10). Dosing was initiated according to the treatment plan summarized in Tables 1 and 2. Vehicle 1 (PBS) and SEQ ID NO: 2 at 3 mg/kg were dosed subcutaneously (s.c.) in the dorsal scapular region; vehicle 2 and lenvatinib were dosed orally (p.o.) for 28 days (qd×28); all agents were administered in a volume of 10 mL/kg (0.2 mL/20 g mouse) scaled to the body weights of each animal.

Group 1 received Vehicle 1 s.c. on Days 1, 4, 7, 10, 13, 16 and 19 and Vehicle 2 p.o. qd×28.

Group 2 received Vehicle 1 s.c. on Days 1, 4, 7, 10, 13, 16 and 19 and 10 mg/kg lenvatinib p.o. qd×28.

Group 3 received Vehicle 1 s.c. on Days 1, 4, 7, 10, 13, 16 and 19 and 30 mg/kg lenvatinib p.o. qd×28.

Group 4 received Vehicle 1 s.c. on Days 1, 4, 7, 10, 13, 16 and 19 and 100 mg/kg lenvatinib p.o. qd×28.

Group 5 received 3 mg/kg SEQ ID NO: 2 s.c. on Days 1, 4, 7, 10, 13, 16 and 19 and Vehicle 2 p.o. qd×28.

Group 6 received 3 mg/kg SEQ ID NO: 2 s.c. on Days 1, 4, 7, 10, 13, 16 and 19 and 10 mg/kg lenvatinib p.o. qd×28

Sampling

Two hours post first dose, blood was collected under no anesthesia from Animals 1-5 in Groups 2, 3, 4, and 6. Via mandibular bleeds, 0.25 mL of blood was collected and processed for plasma in anti-coagulant-K2EDTA. Samples were snap frozen and kept at shipping condition of −80° C. on dry ice.

Tumor Growth Delay Endpoint

The study endpoint was a tumor volume of 1000 mm3 or Day 53, whichever came first. Each animal was euthanized for tumor progression (TP) when its tumor reached the volume endpoint. The time to endpoint (TTE) for each animal was calculated with the following equation:

$$TTE(\text{days}) = \frac{\log_{10}(endpoint volume, \text{mm}^3) - b}{m}$$

where b is the intercept and m is the slope of the line obtained by linear regression of log-transformed tumor growth data set. The data set is comprised of the first observation that exceeded the study endpoint volume and the three consecutive observations that immediately preceded the attainment of the endpoint volume. Any animal that did not reach tumor volume endpoint was euthanized at the end of the study and assigned a TTE value equal to the last day of the study. In instances in which the log-transformed calculated TTE preceded the day prior to reaching endpoint or exceeded the day of reaching tumor volume endpoint, a linear interpolation was performed to approximate the TTE. Any animal determined to have died from treatment-related (TR) causes was assigned a TTE value equal to the day of death, while any animal that died from non-treatment-related (NTR) causes was excluded from the analysis.

Treatment outcome was evaluated from tumor growth delay (TGD), which was defined as the increase in the median TTE for a treatment group compared to the control group:

TGD=T-C, expressed in days, or as a percentage of the median TTE of the control group:

$$\% \ TGD = \frac{T-C}{C} \times 100 \text{ where}$$

T=median TTE for a treatment group,
C=median TTE for the control group.

Median Tumor Volume (MTV) and Criteria for Regressions

Treatment efficacy may also be determined from the tumor volumes of animals remaining in the study on the last day and from the number and magnitude of regression responses. The MTV (n) is defined as the median tumor volume on the final day in the number of evaluable animals remaining, n, whose tumors have not attained the volume endpoint.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm³ for one or more of these three measurements. In a CR response, the tumor volume is less than 13.5 mm³ for three consecutive measurements during the study. Animals were scored only once during the study for a PR or CR event and only as CR if both PR and CR criteria were satisfied. Any animal with a CR response at the end of the study was additionally classified as a tumor-free survivor (TFS). Animals were monitored for regression responses.

Toxicity

Animals were weighed daily through Day 40 and then twice a week to the end of the study on Day 53. During this time mice were observed for overt signs of any adverse, treatment-related (TR) side effects, and clinical signs were recorded when observed. Individual body weight (BW) was monitored, and any animal with weight loss exceeding 30% for one measurement or exceeding 25% for three consecutive measurements was euthanized as a TR death. Group mean body weight loss was also monitored, and acceptable toxicity was defined as a group mean BW loss of not more than 15% during the study and no more than 10% TR deaths. A death was classified as TR if it was attributable to treatment side effects as evidenced by clinical signs and/or necropsy, and a TR classification was also assigned to deaths by unknown causes within 14 days of the last dose. Deaths were classified as non-treatment-related (NTR) if there was no evidence of treatment-related side effects. NTR deaths were further categorized as follows: NTRa describes deaths due to accidents or human error; NTRm was assigned to deaths thought to result from tumor dissemination by invasion and/or metastasis based on necropsy⁻ results; NTRu describes deaths of unknown causes that lacked available evidence of death related to metastasis, tumor progression, accident or human error. It should be noted that treatment side effects cannot be excluded from deaths classified as NTRu.

Figure 2A:
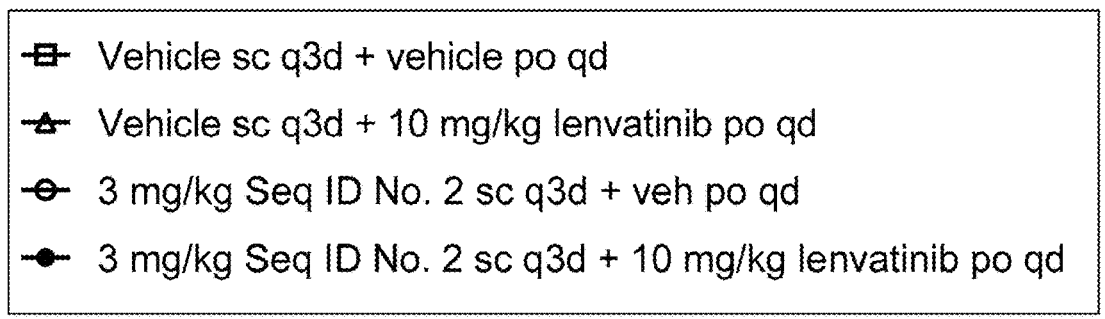
FIG. 2A-FIG. 2B depict the changes in mean tumor volumes ($mm^3$) (FIG. 2A) and percent survival (FIG. 2B)
Figure 2A:
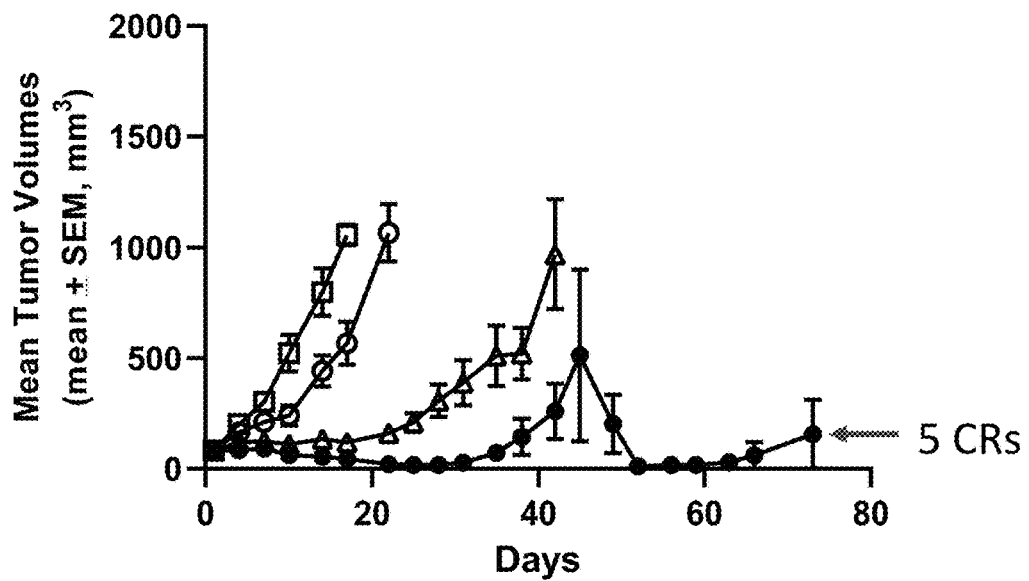

Results:

As shown in FIG. 2A and FIG. 2B, the combination of lenvatinib with the mouse ortholog construct of the fusion protein of SEQ ID NO: 1 (SEQ ID NO: 2) lead to substantial reductions in tumor volume over time and increases in % survival. Moreover, gene expression analysis revealed that the combination stimulated expression of genes associated with immune cytolytic activity (granzyme A and perforin) to a greater level than either compound alone. Expression of the gene Esm1, associated with VEGF activity, was also reduced to a similar or greater extent in the combination compared to each compound alone (FIG. 3). The combination showed improvements that were more than double the effects of each compound individually, suggesting synergistic effects.

The combination of an intermediate-affinity IL-2R-selective cytokine and lenvatinib results in durable dose-dependent antitumor efficacy in a syngeneic mouse model of colon cancer.

Example 2—Anti-VEGF Antibody in Combination with SEQ ID NO: 2

Objectives:

Evaluating the anti-tumor efficacy an anti-VEGF antibody, the fusion protein of SEQ ID NO: 2 (the mouse ortholog construct of the fusion protein of SEQ ID NO: 1), and a combination of the two agents in syngeneic mouse models of cancer (mouse colon cancer cell line, MC38 in female C57BL/6 mice).

The anti-VEGF antibody employed in this study was described in Liang et al (J. Biol. Chem. 281(2): 951-961. 2006), as antibody clone G6-31.

Experimental Design:

The studies will determine if the combination treatment can enhance the efficacy of the monotherapies. These studies include multiple doses of the two agents to define the optimal dose of the combination. Standard readouts will include tumor growth inhibition and survival. Animal models used for this study include MC38 in order to discern if combination with SEQ ID NO: 2 in mouse models will help to augment the sensitivity to the anti-VEGF antibody.

The characteristics of each animal study group, the administration of the test articles and timing, the collection of samples and the overall study design are as shown in Tables 3 and 4:

TABLE 3

Study design

| | | | Treatment Regimen 1 | | | | Treatment Regimen 2 | | |
|---|---|---|---|---|---|---|---|---|---|
| Group | n | Agent | mg/kg | Route | Schedule | Agent | mg/kg | Route | Schedule |
| 1 | 10 | vehicle | — | sc | days 1, 4, 7, 10, 13, 16, 19 | vehicle | — | ip | days 1, 4, 8, 11, 15, 18, 21 |
| 2 | 10 | vehicle | — | sc | days 1, 4, 7, 10, 13, 16, 19 | anti-VEFG-AKM | 1 | ip | days 1, 4, 8, 11, 15, 18, 21 |
| 3 | 10 | vehicle | — | sc | days 1, 4, 7, 10, 13, 16, 19 | anti-VEFG-AKM | 5 | ip | days 1, 4, 8, 11, 15, 18, 21 |

TABLE 3-continued

Study design

| Group | n | Treatment Regimen 1 | | | | Treatment Regimen 2 | | | |
|---|---|---|---|---|---|---|---|---|---|
| | | Agent | mg/kg | Route | Schedule | Agent | mg/kg | Route | Schedule |
| 4 | 10 | vehicle | — | sc | days 1, 4, 7, 10, 13, 16, 19 | anti-VEFG-AKM | 10 | ip | days 1, 4, 8, 11, 15, 18, 21 |
| 5 | 10 | SEQ ID NO: 2 | 3 | sc | days 1, 4, 7, 10, 13, 16, 19 | vehicle | — | ip | days 1, 4, 8, 11, 15, 18, 21 |
| 6 | 10 | SEQ ID NO: 2 | 3 | sc | days 1, 4, 7, 10, 13, 16, 19 | anti-VEFG-AKM | 5 | ip | days 1, 4, 8, 11, 15, 18, 21 |

Table 1 displays the study design as of Day 1 of the study.
vehicle = PBS

TABLE 4

Response summary of Example 2 study

| Group | n | Treatment Regimen | | | | Median | | | Statistical Significance | |
|---|---|---|---|---|---|---|---|---|---|---|
| | | Agents | mg/kg | Route | Schedule | TTE | T − C | % TGD | vs G1 | vs G2 |
| 1 | 10 | vehicle | — | sc | days 1, 4, 7, 10, 13, 16, 19 | 16.2 | — | — | — | *** |
| | | vehicle | — | ip | days 1, 4, 8, 11, 15, 18, 21 | | | | | |
| 2 | 8 | vehicle | — | sc | days 1, 4, 7, 10, 13, 16, 19 | 20.8 | 4.6 | 28 | *** | — |
| | | anti-VEGF-AKM | 1 | ip | days 1, 4, 8, 11, 15, 18, 21 | | | | | |
| 3 | 9 | vehicle | — | sc | days 1, 4, 7, 10, 13, 16, 19 | 23.9 | 7.7 | 48 | *** | ns |
| | | anti-VEGF-AKM | 5 | ip | days 1, 4, 8, 11, 15, 18, 21 | | | | | |
| 4 | 10 | vehicle | — | sc | days 1, 4, 7, 10, 13, 16, 19 | 26.2 | 10.0 | 62 | *** | ** |
| | | anti-VEGF-AKM | 10 | ip | days 1, 4, 8, 11, 15, 18, 21 | | | | | |
| 5 | 10 | SEQ ID NO: 2 | 3 | sc | days 1, 4, 7, 10, 13, 16, 19 | 21.7 | 5.5 | 34 | *** | — |
| | | vehicle | — | ip | days 1, 4, 8, 11, 15, 18, 21 | | | | | |
| 6 | 9 | SEQ ID NO: 2 | 3 | sc | days 1, 4, 7, 10, 13, 16, 19 | 38.4 | 22.2 | 137 | *** | — |
| | | anti-VEGF-AKM | 5 | ip | days 1, 4, 8, 11, 15, 18, 21 | | | | | |

| Group | Statistical Significance | | MTV (n) | Regressions | | | Mean BW | Deaths | |
|---|---|---|---|---|---|---|---|---|---|
| | vs G4 | vs G6 | Day 47 | PR | CR | TFS | Nadir | TR | NTRu |
| 1 | *** | *** | — | 0 | 0 | 0 | — | 0 | 0 |
| 2 | ** | — | — | 0 | 0 | 0 | — | 0 | 2 |
| 3 | ns | *** | — | 0 | 0 | 0 | −0.5% Day 2 | 0 | 1 |
| 4 | — | — | — | 0 | 0 | 0 | −1.2% Day 2 | 0 | 0 |
| 5 | — | *** | — | 0 | 0 | 0 | — | 0 | 0 |
| 6 | — | — | 333 (2) | 0 | 1 | 1 | — | 0 | 1 |

Table 2 displays the scheduled treatment regimen at completion of the study.
vehicle = PBS
Study Endpoint = 1000 mm$^3$;
Study Duration = 47 Days
n = number of animals in a group not dead from accidental or unknown causes, or euthanized for sampling
TTE = time to endpoint,
T − C = difference between median TTE (days) of treated versus control group,
% TGD = [(T − C)/C] × 100
The maximum T − C in this study is 30.8 days (190%), compared to Group 1
Statistical Significance (Logrank test):
ne = not evaluable,
ns = not significant,
* = P < 0.05,
** = P < 0.01,
*** = P < 0.001, compared to Group 1 or group indicated
MTV (n) = median tumor volume (mm$^3$) for the number of animals on the Day of TGD analysis (excludes animals with tumor volume at endpoint)
PR = partial regressions;
CR = total number complete regressions;
TFS = tumor free survivors, i.e., tumor volume ≤ 13.5 mm3 for the final three measurements of the study
Mean BW Nadir = lowest group mean body weight, as % change from Day 1;
— indicates no decrease in mean body weight was observed
TR = treatment-related death;
NTRu = non-treatment-related death due to unknown etiology Therapeutic Agents SEQ ID NO: 2 was prepared as described in Example 1.

The anti-VEGF antibody (anti-VEGF-AKM) stock solution was thawed and aliquoted for use during the week. On each day of dosing aliquots were diluted in vehicle (sterile PBS, pH 7.4) and held at 4° C. protected from the light until dosing to obtain dosing solutions 1.0, 0.5, and 0.1 mg/mL, which delivered 10, 5, 1 mg/kg when administered in a dosing volume of 10 mL/kg adjusted to the body weight of each animal.

Treatment

On Day 1 of the study, mice bearing established subcutaneous MC38 tumors were sorted into six groups (n=10). Dosing was initiated according to the treatment plan summarized in Table 3, and the final dosing regimens are summarized in Table 4. Vehicle and SEQ ID NO: 2 at 3 mg/kg were dosed subcutaneously (s.c.) in the dorsal scapular region on Days 1, 4, 7, 10, 13, 16, 19; vehicle and Anti-VEGF-AKM were dosed intraperitoneally (i.p.) on Days 1, 4, 8, 11, 15, 18, 21; all agents were administered in a volume of 10 mL/kg (0.2 mL/20 g mouse) scaled to the body weights of each animal.

Group 1 received vehicle on both schedules.

Group 2 received vehicle in combination with 1 mg/kg Anti-VEGF-AKM.

Group 3 received vehicle in combination with 5 mg/kg Anti-VEGF-AKM.

Group 4 received vehicle in combination with 10 mg/kg Anti-VEGF-AKM.

Group 5 received 3 mg/kg SEQ ID NO: 2 in combination with vehicle.

Group 6 received 3 mg/kg SEQ ID NO: 2 in combination with 5 mg/kg Anti-VEGF-AKM.

Sampling

Four hours post first dose, four hours post Anti-VEGF-AKM (Day 18), and fourteen days post last Anti-VEGF-AKM (Day 35) blood was collected under no anesthesia from all animals in Groups 2, 3, 4, and 6. Via mandibular bleeds, 0.2 mL of blood was collected and processed for serum snap frozen and kept at −80° C. shipping condition on dry ice. At endpoint, tumors were collected from 5 animals per group. The tumors were weighed and preserved via RNA-later and kept at −4° C. shipping condition on cold packs.

Figure 1A:
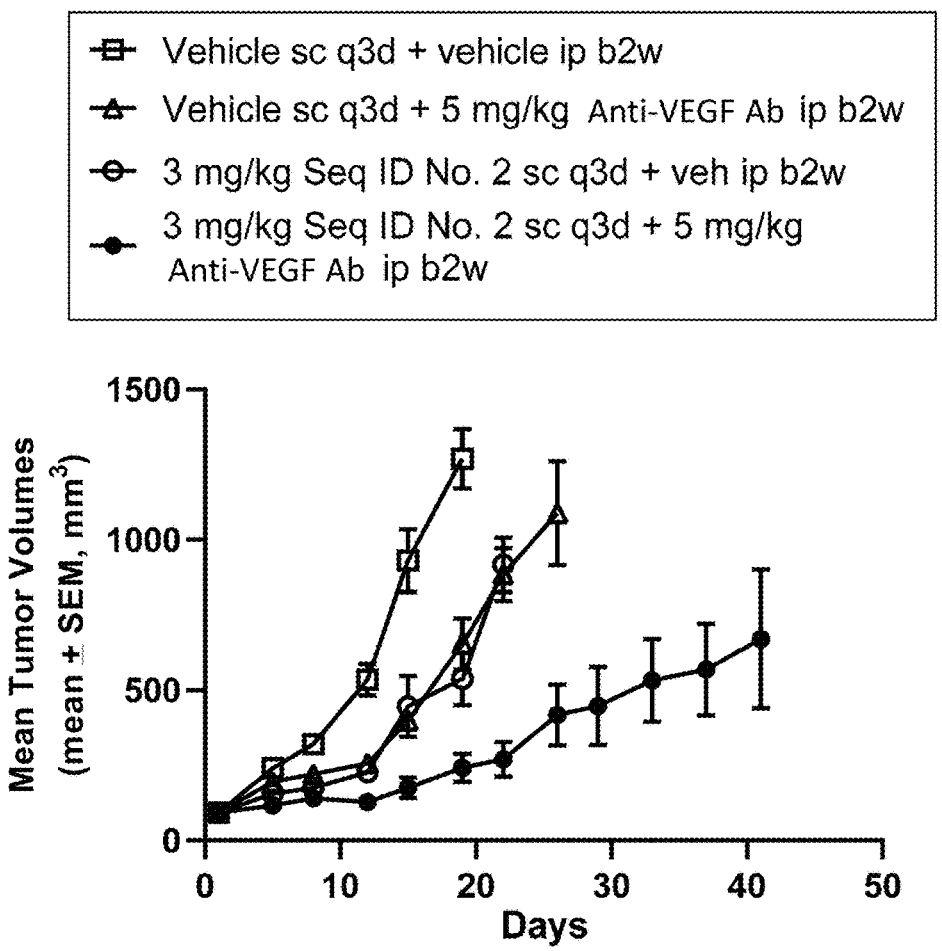
FIG. 1A-FIG. 1B depict the changes in mean tumor volumes ($mm^3$) (FIG. 1A) and percent survival (FIG. 1B) over a period of days in mice implanted with MC38 tumor cells and thereafter treated with various doses of SEQ ID NO: 2, the murine surrogate of SEQ ID NO: 1 and/or the anti-VEGF antibody G6-31, as described in Liang et al. (J. Biol. Chem. 281(2): 951-961. 2006).
Figure 1B:
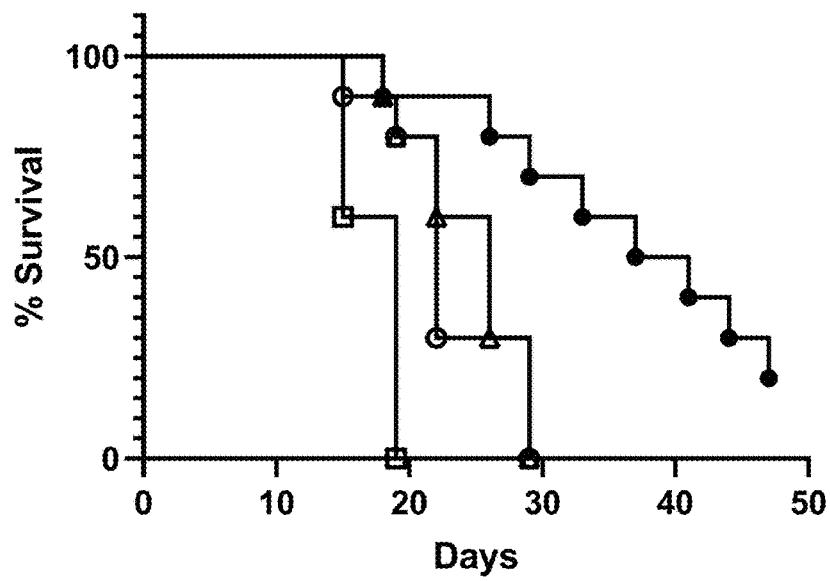
Figure 2B:
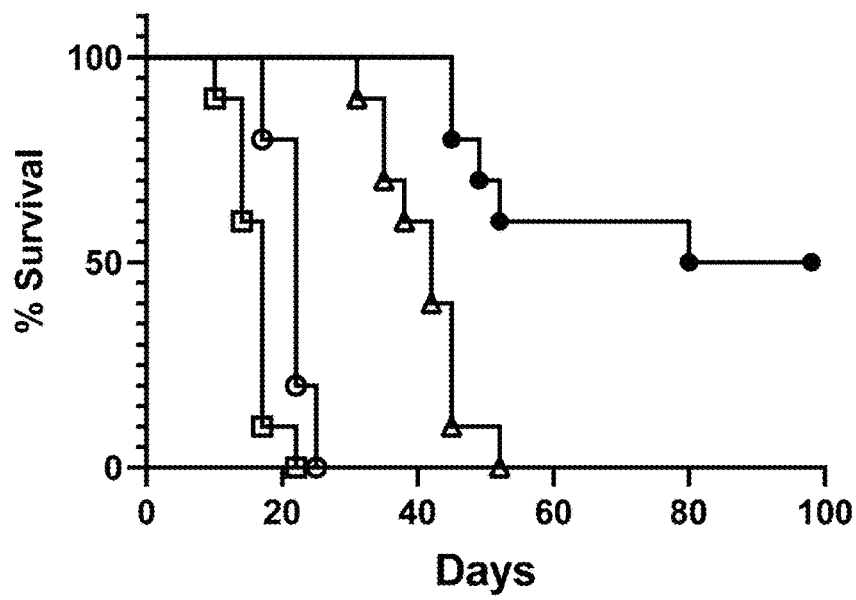

Results:

As shown in FIG. 1A and FIG. 1B, the combination of an anti-VEGF antibody with the mouse ortholog construct of the fusion protein of SEQ ID NO: 1 (SEQ ID NO: 2) lead to substantial reductions in tumor volume over time and increases in % survival. The combination showed improvements that were more than double the effects of each compound individually, suggesting synergistic effects.

The combination of an intermediate-affinity IL-2R-selective cytokine and an anti-VEGF antibody results in durable dose-dependent antitumor efficacy in a syngeneic mouse model of colon cancer.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. A method of treating cancer in a patient in need thereof, the method comprising:
   i) Administering to the patient a therapeutically effective amount of a fusion protein of SEQ ID NO: 1 and
   ii) Administering to the patient a therapeutically effective amount of lenvatinib;
   wherein step (i) is carried out simultaneously with step (ii).

2. The method of claim 1, wherein an effective amount of the fusion protein of SEQ ID NO: 1 is an amount effective to activate the IL-2 intermediate receptor, IL-2Rβγ.

3. The method of claim 1, wherein the fusion protein of SEQ ID NO: 1 is administered by intravenous or subcutaneous injection.

4. The method of claim 1, wherein the lenvatinib inhibits more than one receptor tyrosine kinase.

5. The method of claim 4, wherein the lenvatinib inhibits one or more of the following receptor tyrosine kinases: vascular endothelial growth factor receptors types 1, 2, and 3; platelet derived growth factor receptors, types alpha and beta platelet derived growth factor receptors, and fibroblast growth factor receptors, types 1, 2, and 3.

6. The method of claim 1, wherein lenvatinib is administered orally.

7. The method of claim 1, wherein the combination of steps (i) and (ii) results in an increase in CD8+ T cells in the tumors and spleen of the patient as compared to administration of a therapeutically effective amount of the fusion protein of SEQ ID NO: 1 as a monotherapy or administration of a therapeutically effective amount of the lenvatinib as a monotherapy.

8. The method of claim 7, wherein the increase in CD8+ T cells is at least 2-fold greater as compared to administration of a therapeutically effective amount of the fusion protein of SEQ ID NO: 1 as a monotherapy or administration of a therapeutically effective amount of the lenvatinib as a monotherapy.

9. The method of claim 7, wherein there is no increase in CD4+ T regulatory ($T_{regs}$) cells or conventional CD4+ T cells in the patient.

10. The method of claim 1, wherein the combination of steps (i) and (ii) results in an increase in CD8+ T cells and dendritic cells in the tumors and spleen of the patient and a decrease in tumor associated macrophages in the patient as compared to administration of a therapeutically effective amount of the fusion protein of SEQ ID NO: 1 as a monotherapy or administration of a therapeutically effective amount of the lenvatinib as a monotherapy.

11. The method of claim 10, wherein there is no increase in CD4+ T regulatory ($T_{regs}$) cells in the patient.

12. The method of claim 11, wherein the combination of steps (i) and (ii) results in an increase in CD8+ T cells and dendritic cells in the tumors and spleen of the patient and a decrease in tumor-associated macrophages in the patient as compared to administration of a therapeutically effective amount of the fusion protein of SEQ ID NO: 1 as a monotherapy or administration of a therapeutically effective amount of the lenvatinib as a monotherapy.

13. The method of claim 1, wherein the progression free survival of the patient is increased by at least about 10% as compared to administration of a therapeutically effective amount of the fusion protein of SEQ ID NO: 1 as a monotherapy or administration of a therapeutically effective amount of the lenvatinib as a monotherapy.

14. The method of claim 1, wherein the combination of steps (i) and (ii) results in greater expression of genes associated with cytotoxic immune cell function, T cell activation, and antigen presentation as compared to administration of a therapeutically effective amount of the fusion protein of SEQ ID NO: 1 as a monotherapy or administration of a therapeutically effective amount of the lenvatinib as a monotherapy.

15. The method of claim 1 wherein the combination of steps (i) and (ii) results in a decrease in Esm1 expression, and increased expression of Type I interferon and Type II interferon-associated genes as compared to administration of a therapeutically effective amount of the fusion protein of SEQ ID NO: 1 as a monotherapy or administration of a therapeutically effective amount of the lenvatinib as a monotherapy.

16. The method of claim 1, wherein the combination of steps (i) and (ii) results in changes in expression of a greater total number of genes as compared to administration of a therapeutically effective amount of the fusion protein of SEQ ID NO: 1 as a monotherapy or administration of a therapeutically effective amount of the lenvatinib as a monotherapy.

* * * * *